US008260035B2

(12) United States Patent
Tek et al.

(10) Patent No.: US 8,260,035 B2
(45) Date of Patent: Sep. 4, 2012

(54) THRESHOLD DETERMINATION IN AN INSPECTION SYSTEM

(75) Inventors: Mehmet Tek, Quincy, MA (US); Timothy Tiemeyer, Providence, RI (US); Andrey Vertikov, Westwood, MA (US)

(73) Assignee: KLA-Tencor Corporation, Milpitas, CA (US)

( * ) Notice: Subject to any disclaimer, the term of this patent is extended or adjusted under 35 U.S.C. 154(b) by 832 days.

(21) Appl. No.: 11/525,527

(22) Filed: Sep. 22, 2006

(65) Prior Publication Data

US 2008/0075353 A1 Mar. 27, 2008

(51) Int. Cl.
*G06K 9/00* (2006.01)

(52) U.S. Cl. ........ 382/152; 382/100; 382/141; 382/149; 382/145

(58) Field of Classification Search .................. None
See application file for complete search history.

(56) References Cited

U.S. PATENT DOCUMENTS

| | | | | | |
|---|---|---|---|---|---|
| 5,822,055 | A | * | 10/1998 | Tsai et al. | 356/237.1 |
| 6,002,122 | A | * | 12/1999 | Wolf | 250/207 |
| 6,097,428 | A | * | 8/2000 | Wu et al. | 348/126 |
| 6,724,473 | B2 | * | 4/2004 | Leong et al. | 356/237.2 |
| 7,271,891 | B1 | * | 9/2007 | Xiong et al. | 356/237.4 |
| 7,356,430 | B2 | * | 4/2008 | Miguelanez et al. | 702/108 |
| 7,436,508 | B2 | * | 10/2008 | Wolters et al. | 356/237.5 |
| 7,437,271 | B2 | * | 10/2008 | Tabor | 702/183 |
| 7,440,093 | B1 | * | 10/2008 | Xiong et al. | 356/237.4 |
| 7,557,910 | B2 | * | 7/2009 | Baran et al. | 356/237.2 |
| 7,639,863 | B2 | * | 12/2009 | Isomura | 382/144 |
| 2002/0040968 | A1 | * | 4/2002 | Black et al. | 250/393 |
| 2002/0114506 | A1 | * | 8/2002 | Hiroi et al. | 382/149 |
| 2003/0045100 | A1 | * | 3/2003 | Saka et al. | 438/689 |
| 2003/0219153 | A1 | * | 11/2003 | Levin et al. | 382/141 |
| 2004/0105578 | A1 | * | 6/2004 | Tsuchiya et al. | 382/144 |
| 2005/0165567 | A1 | * | 7/2005 | Inatsune | 702/66 |
| 2005/0278597 | A1 | * | 12/2005 | Miguelanez et al. | 714/738 |
| 2006/0028779 | A1 | * | 2/2006 | Bax et al. | 361/93.1 |
| 2007/0011513 | A1 | * | 1/2007 | Biswas et al. | 714/722 |
| 2007/0012867 | A1 | * | 1/2007 | Wolters et al. | 250/214 R |
| 2007/0013899 | A1 | * | 1/2007 | Wolters et al. | 356/237.2 |
| 2008/0075353 | A1 | * | 3/2008 | Tek et al. | 382/145 |

* cited by examiner

*Primary Examiner* — Chan S Park
*Assistant Examiner* — Avinash J Yentrapati
(74) *Attorney, Agent, or Firm* — Luedeka Neely Group, P.C.

(57) ABSTRACT

A method and system for inspecting a surface of a semiconductor workpiece comprises providing a surface inspection system and using the surface inspection apparatus to cause laser light to impinge upon a test location on the workpiece surface and thereby cause the laser light to emerge from the surface as returned light comprising at least one of reflected light and scatter light; collecting the returned light and generating a signal from the returned and collected light, the signal comprising a signal value representative of a characteristic of the workpiece surface at the test location; providing a plurality of threshold candidates and causing the surface inspection system to select a threshold from among the plurality of threshold candidates; comparing the threshold to the signal value to obtain a difference value; using the difference value to assess the characteristic of the workpiece surface at the test location; and using the surface inspection system to automatically cause the method to be repeated for a plurality of test locations on the workpiece surface.

10 Claims, 13 Drawing Sheets

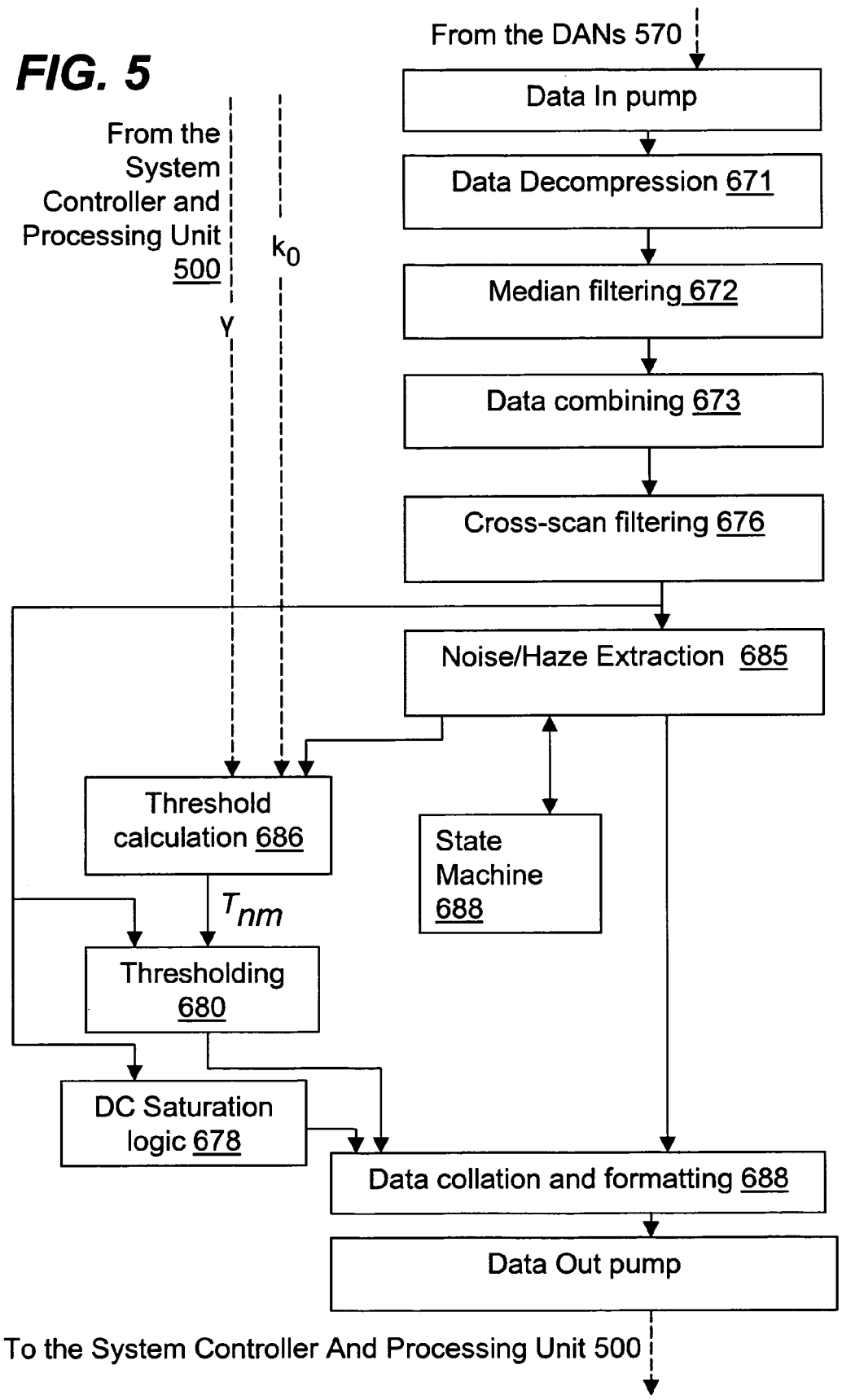

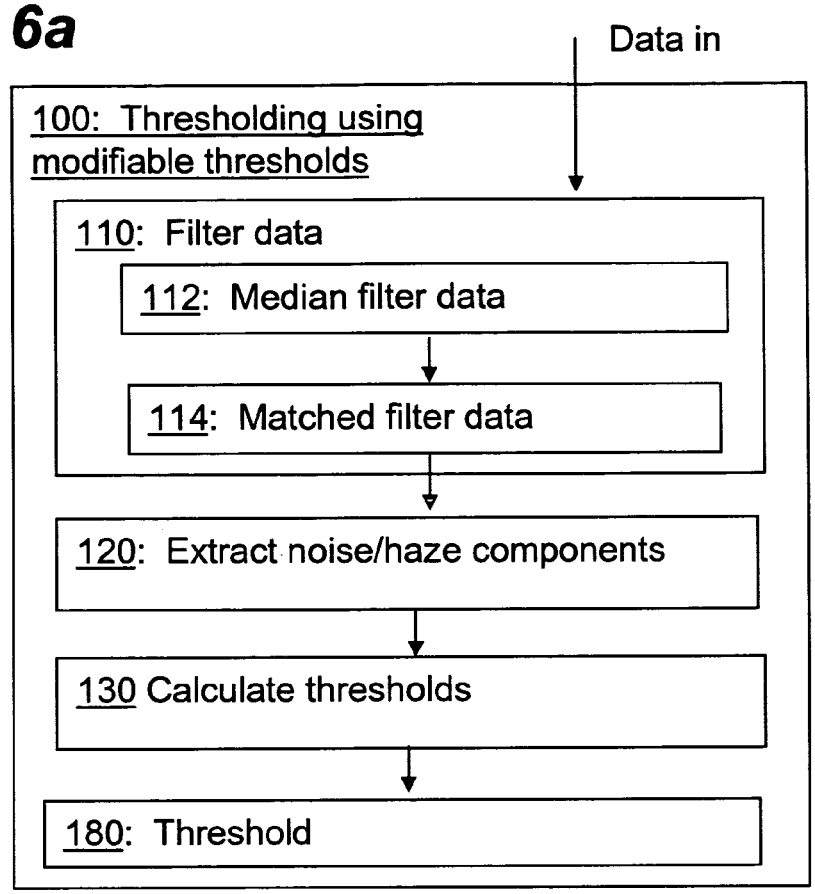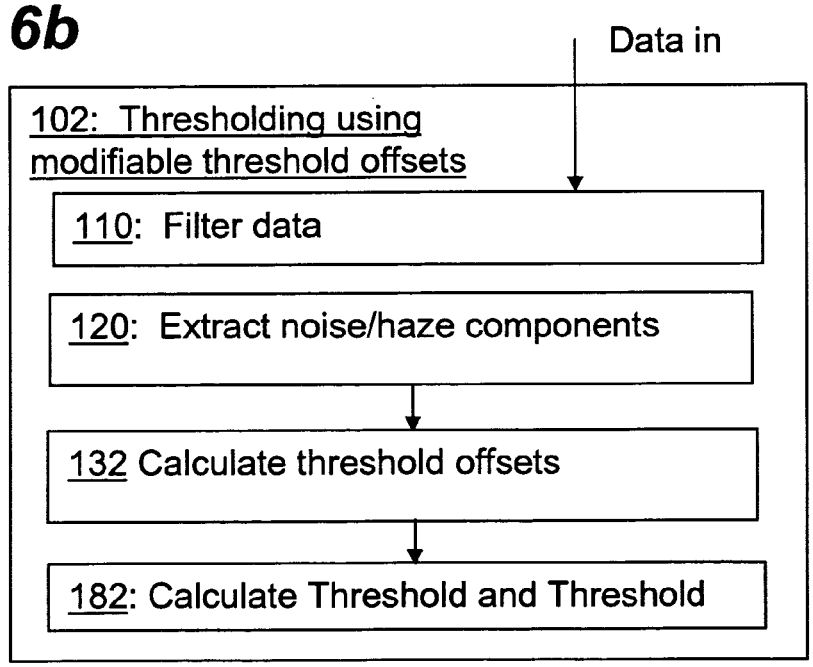

| | Composite | |
|---|---|---|
| | Size | LLS |
| 1 | 0.050 - 0.060 | 225 |
| 2 | 0.060 - 0.070 | 443 |
| 3 | 0.070 - 0.080 | 71 |
| 4 | 0.080 - 0.090 | 22 |
| 5 | 0.090 - 0.100 | 12 |
| 6 | 0.100 - 0.200 | 29 |
| 7 | 0.200 - 0.300 | 6 |
| 8 | 0.300 - 1.000 | 8 |
| 9 | 1.000 - All | 16 |
| 10 | Sum | 832 |

THRESHOLD DETERMINATION IN AN INSPECTION SYSTEM

CROSS-REFERENCE TO RELATED APPLICATION

N/A

STATEMENT REGARDING FEDERALLY SPONSORED RESEARCH OR DEVELOPMENT

N/A

BACKGROUND OF THE INVENTION

1. Field of the Invention

The present invention relates to technology for the inspection of a surface or surfaces of a workpiece, such as a semiconductor wafer, chip, or the like. More particularly, it relates to apparatus and methods for inspection of such workpiece surfaces using electromagnetic energy, e.g., light, to scan the surface to obtain characteristics of the surface or other information concerning the surface.

2. Description of the Related Art

There are a number of applications in which it is desirable or advantageous to inspect a surface or surfaces of a workpiece to obtain information about the characteristics and/or condition of that surface or surfaces. Examples of workpieces amenable to such application would include, for example, bare or unpatterned semiconductor wafers, semiconductor wafers with an applied film or films, patterned wafers, and the like. Characteristics and conditions of the surface that are commonly of interest include surface geometry such as flatness, surface roughness, etc., and/or the presence of defects, such as particles, crystal originated pits ("COPs") and crystalline growths. Given the increasing drive over the years to reduce device size and density, there has been a need for increasing control over surface characteristics or properties at reduced dimensions, and an increasing demand for a reduction in the size of defects, the types of defects that are permissible, etc. Correspondingly, there is an enhanced need for resolution, detection and characterization of small surface characteristics, properties, defects, etc., and an enhanced need for increased measurement sensitivity and classification capability.

In the face of this demand, a number of systems and methods have emerged to provide this capability. One such system, for example, is disclosed in U.S. patent application Ser. No. 11/311,905 (the "'905 application"), which is assigned to ADE Optical Systems Corporation of Westwood, Mass. The '905 application discloses a surface inspection system and related methods for inspecting the surface of a workpiece, wherein a beam of laser light is directed to the surface of the workpiece, the light is reflected off the surface, and both scattered and specular light are collected to obtain information about the surface. An acousto-optical deflector is used to scan the beam as the wafer is moved, for example, by combined rotation and translation, so that the entire surface of the workpiece is inspected.

As our understanding of the physics and phenomenology of optical scattering from surfaces has improved, a capability has been developed and refined in which detailed and high resolution information about defects on the surface can be ascertained. These phenomena largely are obtained from the optical energy that is scattered by the surface, as opposed to the energy in the main reflected beam or the "specular beam." Examples of systems and methods that provide such defect detection capability include not only the '905 application but also U.S. Pat. No. 5,712,701, U.S. Pat. No. 6,118,525 and U.S. Pat. No. 6,292,259, all of which are assigned to ADE Optical Systems Corporation and all of which are herein incorporated by reference as if fully set forth herein. Systems designed according to these patents have performed admirably and provided major advances over their predecessors. As the drive to smaller device dimensions and higher device densities has continued, however, the need also has continued for the ability to resolve and classify even smaller and smaller surface properties, defects, etc. A need also has developed to detect and characterize a greater range of surface characteristics and defects in terms of the types of defects, their extent or range, etc.

In the surface inspection systems mentioned above, laser light traverses a surface of a semiconductor wafer and generates reflected and scatter light. One technique for identifying a defect on the surface of a semiconductor wafer comprises developing a filtered voltage signal that is representative of the intensity of the reflected light and the scatter light, and comparing the filtered signal to a defect detection threshold. The threshold is a voltage value that represents a scatter light intensity that may be expected to be representative of a characteristic such as an actual defect. Non-zero filtered voltage signal levels less than the defect detection threshold are likely to be non-defect events, such as system noise, surface roughness, Rayleigh scatter, or other phenomenon.

A trade-off exists between the probability of defect detection and the reliability of defect detection in scattered light measurements. As the user sets the defect detection threshold lower, the surface inspection system is more likely to detect a greater number of defects, because scatter light intensity readings associated with defects having smaller sizes will be also be classified as defect events. However, as the threshold is set lower, the probability increases that an apparent defect detection actually constitutes a false identification of a defect, also known as a "false alarm".

A defect detection threshold may be selected based on the extent of confidence that is desired in the system's defect detection capabilities. In the past, the defect detection threshold has been selected with reference to the surface inspection system's ability to reproduce its results, as reflected in a constant false alarm rate (CFAR) value. The CFAR is a constant value, constituting an expected rate of "false alarms" in the voltage signal output of the surface inspection system. At set-up of the surface inspection system, a maximum CFAR is selected to constitute the maximum probability of false defect detection that the user, designer, or operator is willing to accept. The CFAR may then be used to establish the minimum defect size that is detectable by the surface inspection system, given the selection of the CFAR as maximum acceptable probability of false defect detection.

The identification of defect candidates constitutes a forecast that the aberration being analyzed is a defect. The forecast may be simplified into a yes/no statement (categorical forecast; in this case "aberration identified as a defect candidate defect"/"not identified as defect candidate"), with the event being forecasted itself being put into one of two categories (defect event/non-defect event)

Let H denote "hits" (i.e., all correct event forecasts—an aberration identified as a defect candidate turns out to be a defect); let F denote "false alarms" (an aberration identified as a defect candidate turns out to be a non-defect event); let M denote "missed forecasts" (an aberration that had not been identified as a defect candidate turned out to be a defect event); and let Z denote correctly forecasted non-defect events. A forecast/verification table would show:

| Forecast/<br>verification | Defect event | Non-defect event |
|---|---|---|
| Defect candidate ID | H (correct forecast) (also known as hit) | F (incorrect forecast) (also known as false alarms, false positive) |
| Not Defect candidate | M (incorrect non-forecast) (also known as false negative or miss) | Z (correct non-forecast) |

Assume altogether N forecasts with H+F+M+Z=N. In a perfect forecast, F and M are zero. The constant false alarm rate, being the fraction of defect candidates that were actually non-defect events; can be calculated using the equation: CFAR=F/N. Thus, CFAR is the fraction of false alarms in the set of all events.

Due to the physics of surface inspection systems, a threshold that has been selected with reference to the CFAR value rarely remains a constant, because a false alarm threshold is a function of the amount of light reflected and scattered from the wafer. However, the amount of light reflected and scattered from a wafer varies from wafer to wafer. Every wafer type reflects different amounts of light. Further, even the same type of wafer from different manufacturers may have considerable differences in the amount of reflected and scattered light. In a scenario in which the amount of reflected and scattered light is subject to change, use of a constant defect detection threshold will result in variation in a system's false defect detection rate, resulting in either identifying an increased number of false defects or failing to identify smaller defects that would otherwise have been reliably measurable. In summary, a lack of confidence can develop in the ability of a surface inspection system to consistently detect defects. The false alarm rate is associated with noise, where noise is defined as one standard deviation from the mean and is derived from variance as, $$\text{Variance} = \sigma^2, \text{ or Noise} = \sqrt{\sigma^2} = \sigma.$$

The false alarm rate is associated with noise, in units of sigma (σ) through the cumulative probability distribution function of a Gaussian distributed random variable. As can be seen in FIG. 15, which shows the functional relationship in graphical form, as the number of false counts decreases, the threshold normalized to the noise standard deviation increases.

False alarm thresholds adjust for the differences in wafer manufacturing process variations and measurement device variations to provide the optimal sensitivity. However, false alarm thresholds may overload the measurement system with unnecessary data when the measured wafers are not of the highest quality, such as reclaim wafers. This overload burdens the machine by slowing it down, and yields large sized wafer maps that have to be stored by the manufacturers. Additional burdens include increases in storage needs, data transport and data management.

Defect detection thresholds may also be selected based on the extent of sensitivity that is desired in the system's defect detection capabilities. In the past, the defect detection threshold has been selected with reference to the surface inspection system's sensitivity to detect aberration that could constitute defect events, as reflected in the surface inspection system's constant sensitivity (CSENS) voltage. A threshold based on the CSENS voltage is representative of the smallest defect size that is detectable given the sensitivity of the surface inspection system.

In practice, it is quite tedious to manually determine false detection rates and set optimal defect size-determined thresholds for every wafer type/batch in a production environment.

OBJECTS OF THE INVENTION

Accordingly, an object of the present invention according to one aspect is to provide apparatus and methods for inspecting a surface of a workpiece with high sensitivity and reliability, e.g., for surface defects.

Another object is to provide apparatus and methods for determining thresholds for use in inspecting a surface of a workpiece that do not cause significant increases in system requirements such as storage needs, data transport and data management.

Another object is to provide apparatus and methods for determining thresholds for use in inspecting a surface of a workpiece that would maintain a system's false defect detection rate at a relatively constant rate.

Another object is to provide apparatus and methods for determining thresholds for use in inspecting a surface of a workpiece that satisfy both user-specified results precision and system sensitivity criteria. A further object is to provide apparatus and methods for determining thresholds for use in inspecting a surface of a workpiece that allows a user to select a user-specified balance of results precision and system sensitivity criteria.

Another object is to provide apparatus and methods for determining thresholds for use in inspecting a surface of a workpiece that are based on the data and inspection system size sensitivity simultaneously.

Additional objects and advantages of the invention will be set forth in the description that follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, systems and methods of inspecting semiconductor wafers are provided to classify wafer defects using a threshold modification technique for surface inspection systems in which laser light traversing a surface of a semiconductor wafer generates reflected and scatter light and in which voltage signals that are representative of the intensity of the reflected light and the scatter light are used to identify characteristics of the surface and characteristics of particles on the surface (such as identification as defect, including type and size). An improved system and method for defect detection comprises comparing a modifiable defect detection threshold against an actual voltage signal to identify defects.

The modifiable threshold is selected using a plurality of threshold setting techniques, the inputs for which may comprise user inputs, the actual voltage signal, and of selected components of the actual voltage signal. In one embodiment, a user input with which the modifiable threshold is selected comprises a voltage that is representative of the smallest defect size that is detectable given the sensitivity of the surface inspection system. In another embodiment, a user input with which the modifiable threshold is selected comprises a maximum acceptable probability of false defect detection.

In another embodiment, the selected components of the actual voltage signal comprise the component of the actual voltage signal attributable to haze (a haze component) and the component of the actual voltage signal attributable to noise (a noise component), and the of the selected components are based on the actual voltage signal and accumulated run-rime statistics, comprising statistics derived from voltage signals produced from earlier scatter light intensity readings of the surface of the wafer.

In another embodiment, an improved system and method for defect detection comprises comparing a defect detection threshold against a test voltage signal associated with a test location on the surface of a workpiece to identify defects at the test location, in which the defect detection threshold is selected from multiple threshold candidates. In one embodiment, the threshold candidates are developed using a plurality of threshold setting techniques. In another embodiment, the threshold is selected by adjusting the threshold automatically by a surface inspection system. In a further embodiment, the threshold is adjusted in response to user inputs and estimates of selected components of the actual voltage signal.

Although a variety of threshold candidates may be used, in one embodiment, a first threshold candidate comprises a size-determined threshold candidate, which comprises a voltage that is representative of the smallest defect size that is detectable given the sensitivity of the surface inspection system. The size-determined threshold candidate could comprise a constant sensitivity (CSENS) voltage value.

In one embodiment, a second threshold candidate comprises a false alarm-based threshold candidate comprising a voltage that is representative of the maximum acceptable probability of false identifications of a defect in the voltage signal output of the surface inspection system. In a further embodiment, the false alarm-based threshold candidate comprises a statistically determined false-alarm based threshold candidate comprising a voltage based on run-time statistics derived from the voltage signals associated with an area of the workpiece surface under examination.

In surface inspection systems in which laser light traversing a surface of a semiconductor wafer generates reflected and scatter light and in which voltage signals that are representative of the intensity of the reflected light and the scatter light are used to identify characteristics of the surface, an improved system and method for defect detection comprises comparing a test voltage signal associated with a test location on the surface of a workpiece to identify defects at the test location against a statistically determined false alarm-based threshold comprising a false alarm-based threshold voltage based on statistics derived from voltage signals produced from scatter light intensity readings of the surface of the wafer. In another embodiment, the statistically determined false alarm-based threshold comprises a threshold based on the statistics and a selected maximum acceptable probability false identifications of a defect in the voltage signal output of the surface inspection system. In another embodiment, the statistics comprise a component of the actual voltage signal attributable to haze (a haze component) and a component of the actual voltage signal attributable to noise (a noise component), and the estimates of the selected components are based on the actual voltage signal and accumulated run-time statistics.

In a further embodiment, the current invention comprises the use by a surface inspection system of more than one tier of threshold to identify defect candidates, e.g., in which a first tier $T_1$ of thresholding is used to identify a first group of defect candidates and a second tier $T_2$ of thresholding is used to identify a second group of defect candidates. In a further embodiment, the current invention comprises using multiple tiers of thresholding to conduct defect identification using a plurality of inspection sensitivities in order to accommodate the identification of a plurality of defect types which differ in system sensitivity and identification precision requirements.

In a further embodiment of the current invention a system and method are provided for assessing the capability of a multi-channel surface inspection system to analyze a workpiece to selected defect size identification specifications, by measuring local area noise levels for each channel and establishing detection limits for desired measurement confidence for each channel during acquisition of wafer data based on the local area noise levels. In a further embodiment, the system and method further comprises developing mean haze and local area averages for variance for each channel as wafer data is acquired.

In a further embodiment of the current invention, a system and method is provided for assessing the capability of a multi-channel surface inspection system to analyze a workpiece to selected defect size identification specifications, by comparing channel-specific statistically determined false alarm-based threshold values for a portion of the workpiece to a specified minimum defect size, testing the suitability of the surface inspection system suitable to analyze the workpiece if the specified minimum defect size exceeds a selected number of the channel-specific statistically-determined false alarm-based threshold values. In a further embodiment, testing the suitability of the surface inspection system comprises establishing suitability if the specified minimum defect size exceeds at least one of the channel-specific statistically determined false alarm-based threshold values.

In a further embodiment, a method for inspecting a surface of a semiconductor workpiece comprises providing a surface inspection system and using the surface inspection apparatus to cause laser light to impinge upon a test location on the workpiece surface and thereby cause the laser light to emerge from the surface as returned light comprising at least one of reflected light and scatter light; collecting the returned light and generating a signal from the returned and collected light, the signal comprising a signal value representative of a characteristic of the workpiece surface at the test location; providing a plurality of threshold candidates and causing the surface inspection system to select a threshold from among the plurality of threshold candidates; comparing the threshold to the signal value to obtain a difference value; using the difference value to assess the characteristic of the workpiece surface at the test location; and using the surface inspection system to automatically cause the method to be repeated for a plurality of test locations on the workpiece surface. The collected and returned light consists of scatter light and of reflected light.

In a further embodiment, the providing of the plurality of threshold candidates comprises providing at least one of the threshold candidates using an estimate of the signal value. In a further embodiment, the providing of the threshold candidates comprises using statistics based upon a plurality of signal values for a corresponding plurality of test locations on the workpiece surface to provide at least one of the threshold candidates. In a further embodiment, the providing of the threshold candidates comprises using a size that is representative of a minimum size expected for the characteristic that is detectable given the sensitivity of the surface inspection system to provide at least one of the threshold candidates. In a further embodiment, the method further comprises using a constant sensitivity (CSENS) value to comprise the at least one threshold candidate.

In a further embodiment, the providing of the threshold candidates comprises using a false alarm-based threshold that is representative of a minimum size expected for the characteristic that is detectable given the sensitivity of the surface inspection system and a desired maximum probability of false identifications of the characteristic in the signal value for the surface inspection system to provide at least one of the threshold candidates.

In a further embodiment, the providing of the threshold candidates comprises using a false alarm-based threshold candidate that is representative of a maximum acceptable probability of false defect detection for the surface inspection system as at least one of the threshold candidates. In a further embodiment, the selection of the threshold comprises using an estimate of the signal value to select the threshold from among the threshold candidates. In a further embodiment, the selection of the threshold comprises using statistics based upon a plurality of signal values for a corresponding plurality of test locations on the workpiece surface. In a further embodiment, the selection of the threshold comprises assigning a value to each of the threshold candidates and selecting the threshold by selecting one of the threshold candidates based on the threshold candidate values. In a further embodiment, the selection of the one of the threshold candidate values comprises selecting a maximum of the threshold candidate values.

In a further embodiment, a system for inspecting a surface of a semiconductor workpiece comprises a laser source that causes a laser light to impinge upon a test location on the workpiece surface and thereby cause the laser light to emerge from the surface as returned light comprising at least one of reflected light and scatter light; a collection subsystem that collects the returned light and generates a signal from the returned and collected light, the signal comprising a signal value representative of a characteristic of the workpiece surface at the test location; a processing device that compares the signal value to a plurality of threshold candidates and selects a threshold from among the plurality of threshold candidates, and that uses the threshold to assess the characteristic of the workpiece surface at the test location; wherein the surface inspection system to automatically analyzes the workpiece surface at a plurality of test locations by making said comparisons at each of the test locations.

In a further embodiment, a method for differentiating noise from particles on a surface of a semiconductor workpiece using a threshold, wherein the threshold is used to assess a characteristic of the workpiece surface at a current test location comprises providing a surface inspection system and using the surface inspection apparatus to cause laser light to impinge upon the current test location on the workpiece surface and thereby cause the laser light to emerge from the surface as returned light comprising at least one of reflected light and scatter light; collecting the returned light and generating a signal from the returned and collected light, the signal comprising a signal value representative of the characteristic of the workpiece surface at the current test location and a plurality of prior signal values representative of the characteristic of the workpiece surface at a corresponding plurality of secondary test locations, wherein the secondary test locations comprise at least one of the current test location and test locations other than the current test location; causing the surface inspection system to select a threshold from among at least one threshold candidate, wherein the at least one threshold candidate is selected based on statistical data for the secondary test locations; comparing the threshold to the signal value to obtain a difference value; using the difference value to assess the characteristic of the workpiece surface at the current test location; and using the surface inspection system to automatically cause the method to be repeated for a plurality of test locations on the workpiece surface. In a further embodiment, the selection of the at least one threshold candidate comprises comparing the signal value with a statistically-determined false alarm-based threshold candidate. In a further embodiment, the statistically-determined false alarm-based threshold candidate is based on a desired maximum probability and statistical characteristics of the signal values for the secondary test locations. In a further embodiment, the signal value comprises a component attributable to haze and a component noise, and the selection of the at least one threshold candidate comprises using at least one of the haze component and the noise component. In a further embodiment, the haze component and the noise component are based on the signal value and accumulated run-time statistics.

In a further embodiment, a system for inspecting a surface of a semiconductor workpiece, wherein the workpiece surface has a characteristic at a current test location, the system comprises a laser source that causes a laser light to impinge upon the current test location on the workpiece surface and thereby cause the laser light to emerge from the surface as returned light comprising at least one of reflected light and scatter light; a collection subsystem that collects the returned light and generates a signal from the returned and collected light, the signal comprising a signal value representative of the characteristic of the workpiece surface at the current test location and a plurality of prior signal values representative of the characteristic of the workpiece surface at a corresponding plurality of secondary test locations, wherein the secondary test locations comprise at least one of the current test location and test locations other than the current test location; and a processing device that selects a threshold from among at least one threshold candidate, compares the threshold to the signal value to obtain a difference value, and uses the difference value to assess the characteristic of the workpiece surface at the current test location, wherein the at least one threshold candidate is selected based on statistical data for the secondary test locations; wherein the surface inspection system automatically analyzes the workpiece surface at a plurality of test locations on the workpiece surface by making said comparisons at each of the test locations.

In a further embodiment, a method for inspecting a surface of a semiconductor workpiece, the method comprises providing a surface inspection system and using the surface inspection apparatus to cause laser light to impinge upon a test location on the workpiece surface and thereby cause the laser light to emerge from the surface as returned light comprising at least one of reflected light and scatter light; collecting the returned light and generating a signal from the returned and collected light, the signal comprising a signal value representative of a characteristic of the workpiece surface at the test location, wherein the signal value comprises raw data comprising a data line comprising a vector of voltage values based on intensity measurements of the returned light at locations on the workpiece surface within the test location and a selected scan line; filtering the raw data; extracting components of the signal value representative of the matched filtered data and attributable to a haze component and a noise component; performing a thresholding calculation; and using the surface inspection system to automatically cause the method to be repeated for a plurality of test locations on the workpiece surface.

In a further embodiment, a method inspecting a surface of a semiconductor workpiece, the method comprises providing a surface inspection system and using the surface inspection apparatus to cause laser light to impinge upon a test location on the workpiece surface and thereby cause the laser light to emerge from the surface as returned light comprising at least one of reflected light and scatter light; collecting the returned light and generating a signal from the returned and collected light, the signal comprising a signal value representative of a characteristic of the workpiece surface at the test location; providing a plurality of threshold candidates in respective tiers and causing the surface inspection system to select a threshold from among the plurality of threshold candidates using the tiers; comparing the threshold to the signal value to obtain a difference value; using the difference value to assess the characteristic of the workpiece surface at the test location; and using the surface inspection system to automatically cause the method to be repeated for a plurality of test locations on the workpiece surface.

In a further embodiment, a first threshold tier is used to identify a first type of the characteristics, and wherein a second threshold tier is used to identify a second type of the characteristics. In a further embodiment, the characteristic being identified comprises defects, and wherein the first type comprises a scratch defect; and the second type comprises a point defect.

In a further embodiment, a method for assessing the capability of a multi-channel surface inspection system to analyze a workpiece to selected defect size identification specifications, the method comprises comparing channel-specific statistically determined false alarm-based threshold values for a portion of the workpiece to a specified minimum defect size, and finding the surface inspection system suitable to analyze the workpiece if the specified minimum defect size exceeds a selected number of the channel-specific false alarm-based threshold values.

In a further embodiment, a method for assessing the capability of a multi-channel surface inspection system to analyze a semiconductor workpiece to selected defect size identification specifications comprises measuring local area noise levels for each channel and establishing detection limits for desired measurement confidence for each channel during acquisition of data on the workpiece based on the local area noise levels.

In a further embodiment, the establishment of detection limits comprises developing mean haze and local area averages for variance for each channel as the data is acquired. In a further embodiment, the finding of the surface inspection system to be suitable comprises finding the surface inspection system to be suitable if the specified minimum defect size exceeds at least one of the channel-specific statistically determined false alarm-based threshold values. In a further embodiment, the comparing of the channel-specific statistically determined false alarm-based threshold values for a portion of the workpiece to associated channel-specific specified minimum defect sizes comprises providing a minimum defect size for each channel. In a further embodiment, the minimum defect size comprises a size-determined threshold value comprising a voltage that is representative of the smallest defect size that is detectable given the sensitivity of the surface inspection system.

BRIEF DESCRIPTION OF THE DRAWINGS

The accompanying drawings, which are incorporated into and constitute a part of the specification, presently preferred embodiments and methods of the invention and, together with the general description given above and the detailed description of the embodiments and methods given below, serve to explain the principles of the invention.

Other advantages will appear as the description proceeds when taken in connection with the accompanying drawings, in which:

FIG. 5 is a functional illustration of the data flow in the Data Reduction Nodes shown in FIG. 3;

FIG. 6a is a functional illustration of a method and subsystem for threshold modification for use in signal processing module or subsystem 19 shown in FIG. 3;

FIG. 6b is a functional illustration of a method and subsystem for threshold modification for use in signal processing module or subsystem 19 shown in FIG. 3, using multiple threshold offsets;

FIG. 8a is a state diagram for use in outlier detection shown in FIG. 6a;

DETAILED DESCRIPTION OF THE PREFERRED EMBODIMENTS AND METHODS

Figure 1:
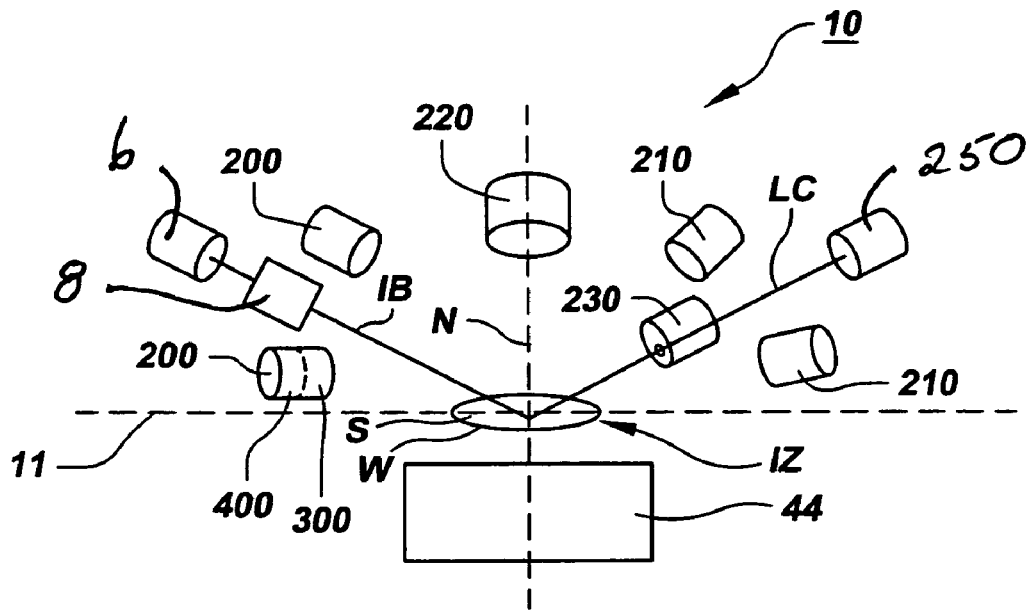
FIG. 1 is a perspective view of components of a surface inspection system according to a presently preferred embodiment of one aspect of the invention.

Reference will now be made in detail to presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

Surface Inspection System

Figure 2:
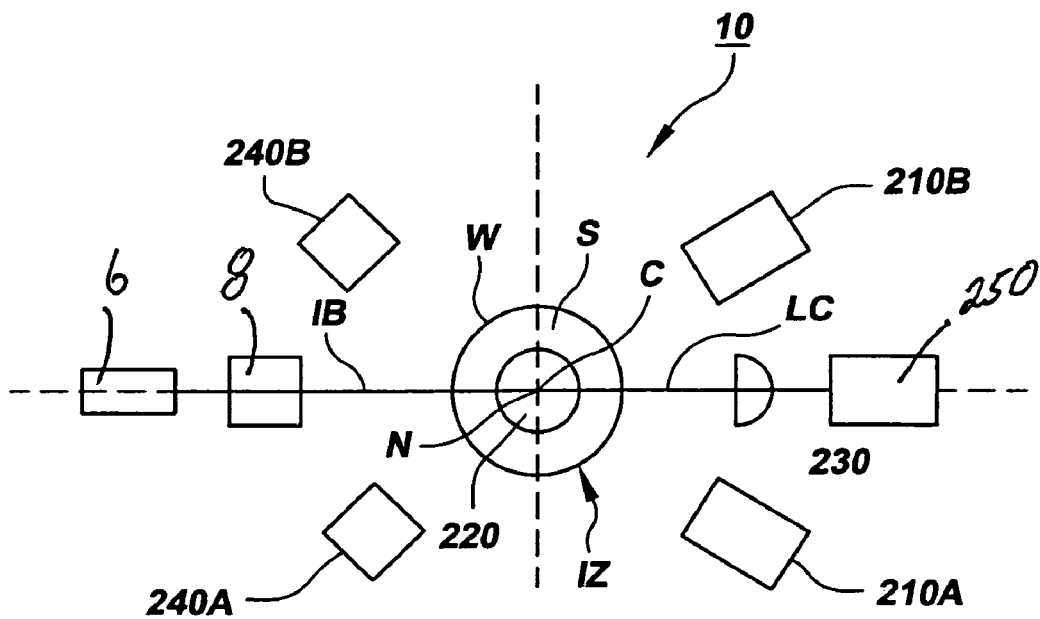
FIG. 2 is a top view of the components of a surface inspection system shown in FIG. 1.

A surface inspection system 10 and related components, modules and subassemblies in accordance with a presently preferred embodiment of and method implementing the invention will now be described. Surface inspection system 10 is designed to inspect a surface S or surfaces of a workpiece W, such as a silicon wafer. More specifically, these illustrative embodiments are adapted for inspection of unpatterned silicon wafers, with or without surface films. Systems according to the invention also would be suitable for inspecting other types of surfaces as well. They are particularly well suited for inspecting optically smooth surfaces that at least partially absorb and scatter the incident beam energy. Examples would include glass and polished metallic surfaces. Wafer W may comprise known wafer designs, such as known 200 millimeter (mm) wafers, 300 mm wafers, and the like. System 10 is shown from various perspectives in FIGS. 1 and 2. FIG. 1 shows a side perspective view block diagram of principal components of the system. FIG. 2 shows the same type of block diagram, but from a top or plan view.

Illumination Subsystem

Preferred surface inspection systems according to this aspect of the invention comprise a laser beam source subsystem 6 for projecting a laser beam and a beam scanning subsystem 8 for receiving the incident beam from the beam source subsystem 6 and scanning the incident beam on the surface S of a workpiece W, a workpiece movement subsystem (not shown) that moves the surface of the workpiece relative to the incident beam, an optical collection and detection subsystem 7, also called a collection module, that collects the reflected beam and photons scattered from the surface of the workpiece and generates signals in response thereto, and a processing subsystem 19 operatively coupled to the collection and detection subsystem 7 for processing the signals.

The manner of moving the workpiece may vary, depending upon the application, the overall system design, and other factors. A number of scan patterns, for example, may be implemented also. Indeed, in some applications it may be desirable to move the beam or scanning subsystem instead of the wafer, i.e., while maintaining the wafer in a stationary location. As implemented in system 10, an internal workpiece handling subsystem 44, also known as a robotic wafer handling subsystem and a motorized γ-θ stage, is provided which comprises a scanner gauge (not shown) and robot (not shown). This subsystem is configured to work in cooperation with an external workpiece handling system (not shown) to receive the workpieces to be inspected. Internal workpiece handling subsystem 44 comprises a motorized linear stage, not shown, and a rotary stage, not shown. It therefore is capable or both rotating and translating the workpiece (γ-θ), for example, to provide a number of scan patterns. This permits the wafer to be scanning in a variety of generally curved paths that provide full and efficient coverage of the entire wafer surface. It enables such scan patterns as concentric cylinder scans, spiral scans and the like. In the preferred embodiments and methods, a "hybrid scan" pattern is used in which the beam travels in a generally helical or Archimedes spiral scan, but in which the beam is oscillated in a series of short scans as the spiral is traced out. This pattern is disclosed in U.S. Pat. No. 5,712,701, No. 6,118,525, and No. 6,292,259, each of which is assigned to ADE Optical Systems Corporation.

With reference to FIGS. 1 and 2, the workpiece W, which in this illustrative example is a semiconductor wafer, resides in an inspection zone IZ within a housing (not shown) during inspection, so that the workpiece under inspection is positioned within this inspection zone IZ. The workpiece W is placed on this stage for inspection and remains there during the inspection. The "incident beam vector" IB is the vector or ray along which an incident beam of laser light propagates between the beam scanning subsystem 8 and the surface S of the workpiece W. The center C of the inspection stage is referred to herein as the "stage center of rotation."

After the incident beam is reflected from the workpiece surface, it propagates along a light channel axis LC. The incident beam vector IB and the light channel axis LC define a plane of incidence. A normal plane is perpendicular to the base plane and the plane of incidence. A vector normal N, corresponding to the z-axis, which is perpendicular to the base plane and which is in the plane of incidence, goes through the stage center of rotation C.

Wafers are inserted into inspection zone IZ for inspection and retrieved from inspection zone IZ after inspection using wafer handling subsystems (not shown). In semiconductor inspection applications and others as well, the handling of the wafers within the housing preferably is done automatically, without contact by human hands, to avoid damaging or impairing the surface, e.g., with smudges, scratches, etc. The wafer handling subsystems provide a plurality of wafers to be inspected. This may be done sequentially or, for system configurations designed to inspect multiple wafers simultaneously, it may provide multiple wafers in parallel.

A robotic wafer handling subsystem places the wafer or wafers on an inspection stage (not shown) within the inspection zone IZ. The robotic wafer handling subsystems may comprise commercially available versions known in the industry. In an illustrative embodiment, the robotic wafer handling subsystem comprises an FX3000/2 robotic wafer handling subsystem, commercially available from Brooks Automation, Inc. (Chelmsford, Mass.). It uses one or more cassettes, with each cassette holding multiple workpieces (up to ten wafers). After placement in the inspection zone IZ, the wafer is automatically aligned, e.g., according to alignment techniques known to those of ordinary skill in the art.

Laser beam source subsystem 6 comprises a beam source such as a laser 6a that projects incident beam IB toward the surface S of the workpiece W. The incident beam IB is formed by laser 6a, which projects a beam having the desired quality and optical properties for the application at hand. The specific characteristics of the laser 6a and the beam it projects may vary from application to application, and are based on a number of factors. In applications involving inspection of semiconductor wafers, suitable lasers comprise Argon lasers having a wavelength of about 488 nm, semiconductor laser diodes at several wavelengths (e.g. GaN (405 μm), AlGaInP (635 nm-670 nm), and AlGaAs in the 780-860 nm range). Other lasers include diode-pumped lasers such as frequency doubled Nd:YVO4, Nd:YAG, and Nd:YLF (532 nm) and quasi-CW diode pumped UV lasers (355 nm). The laser may project a beam that is monochromatic, or which includes a plurality of frequencies or modes, depending upon the specific application, the desired surface features to be measured, etc.

As implemented in this embodiment, the beam source comprises a frequency-doubled Nd:YVO4 laser 6a (Spectra Physics MG-532C) operating at 532 nm frequency. The beam comprises a substantially monochromatic beam having approximately a 532 nm frequency. The beam has a beam size at the laser output of 2 mm (full width at $1/e^2$ level). The beam is outputted from laser with a power of about 1-2 watts and directed toward the beam scanning subsystem 8, which provides for scanning the beam on the surface S of the workpiece W. A number of means may be used to scan the beam in desired fashion. Examples include acousto-optic deflectors (AODs), rotating mirrors, and the like. In the presently preferred embodiments and method implementations, the beam scanning means, not shown, comprises an acousto-optic deflector, not shown, (also known as "acousto-optic deflector", "AO deflector" or "AOD"). The diffracted beam from the AOD defines the target spot position at the surface S of the workpiece W.

The acousto-optic deflector may be an acousto-optic deflector, including but not limited to those commercially available, that is suited for the beam and beam source to be used, the desired scanning parameters (e.g., beam and spot size, scan pattern, scan line dimensions, etc.), and other design requirements and constraints. The AOD according to the presently preferred embodiment and method implementations comprises the ISOMET Model OAD-948R (488 nm) or, alternatively, the ISOMET OAD-971 (532 nm), both of which are available from Isomet Corporation of Springfield, Va.

Optical Collection and Detection Subsystem

After the incident beam is reflected from the workpiece surface, the light comprises reflected light beam and localized scattered light from the surface S of the wafer W. The optical collection and detection subsystem 7 receives the reflected light, which propagates along a light channel axis LC, and detects any losses in light intensity resulting from specular distortion or deflection of the light beam.

The optical collection and detection subsystem 7 comprises components used to collect the beam portions reflected from the surface of the workpiece and scattered from the surface due to surface roughness, defects in the surface, and the like, to detect the collected light and convert it into corresponding signals, e.g., electrical signals, that can be utilized by the processing subsystem 19 to obtain information pertaining to the surface of the workpiece. In the system 10, the signals comprise electrical signals, each of which having a voltage that is proportional to the optical power illuminating optical collection and detection subsystem 7.

The optical collection and detection subsystem 7 comprises light channel system 250 for collecting the beam reflected from the surface of the workpiece into a light channel collector, and dark channel system for collecting the portions of the beam scattered from the surface into a dark channel collector.

As shown in FIG. 1, the dark channel system comprises a series of collection and detection assemblies 200 (also known as collection and detection modules 200), each assembly 200 organized into a collector module 300 (also referred to herein as "collector") for collecting portions of the beam, and a detector module 400 associated therewith.

As shown in FIGS. 1 and 2, the series of collection and detection assemblies 200 comprises a front collection and detection module 230, a center (or central) collection and detection module 220, a pair of wing collection and detection modules 210A, 210B, and a pair of back collection and detection modules 240A, 240B. Although all of the collector-detector assemblies 200 need not necessarily be of the same design and construction, in this preferred embodiment each of them has the same basic design. The front collector 230 differs from the other collectors 210, 220, 240A, 240B in that it is arranged to allow the reflected beam to pass through to the light channel system 250.

The detector module 400 mounted to the collector module 300 has a detector that is sensitive to receive and detect portions of the light beam passing through a lens detector. The detector module 400 has a photo-multiplier tube ("PMT") (not shown), such as the Hamamatsu H6779-20, or an Avalanche Photodiode (APD) Detector (e.g., Advanced Photonix 197-70-74-581).

Signal Processing Subsystem

A processing subsystem or module 19 is operatively coupled to the optical collection and detection subsystem 7 for processing the signals generated by light detection. This processing module 19 performs processing on the signals obtained from the optical collection and detection subsystem 7 to provide desired information concerning the surface S of the workpiece W under inspection, such as its geometry, characteristics, defect information, and the like. The processing system 19 of system 10 comprises a controller such as system controller and processing unit 500.

Figure 3:
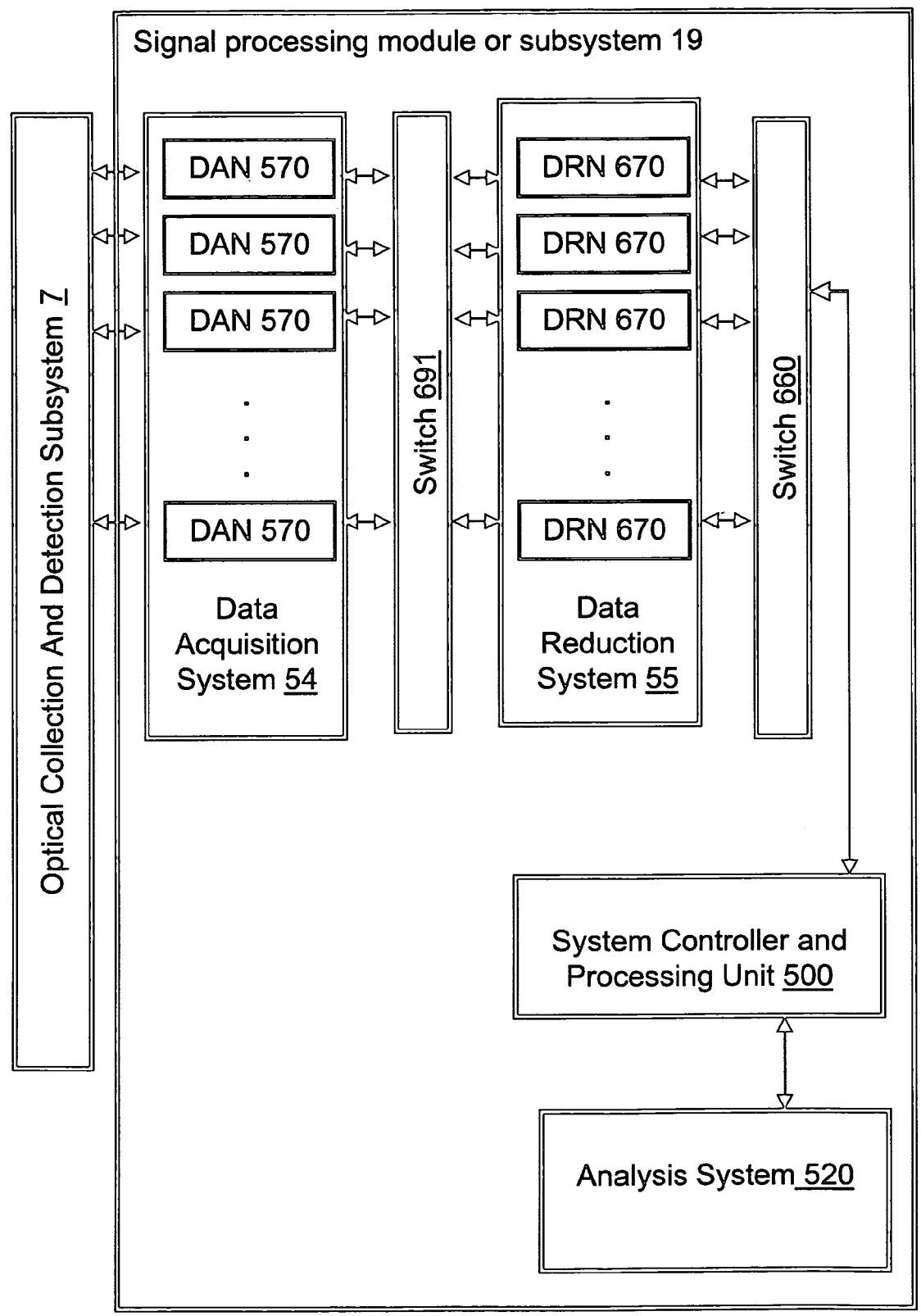
FIG. 3 is a functional illustration of the signal processing module or subsystem 19.

As best illustrated in FIG. 3, the surface inspection system 10 preferably is computer controlled. The system controller and processing unit 500 operates the inspection system, stores and retrieves data generated by the system 10, and performs data analysis preferably responsive to predetermined commands. The relative position of the article being inspected is communicated to the system controller 500 via motors (not shown), and encoders (not shown) mounted thereto.

As understood by those skilled in the art, data signals from the collection and detection assemblies 200 are conventionally electrically communicated to the processing subsystem or module 19, which could comprise digital electronics (not shown) and analog electronics comprising an Analog Combining Board (not shown) for processing the signals, such as that described in the '701 patent. In the system 10, the signals are processed digitally using the system controller and processing unit 500.

As shown in FIG. 3, a data processing subsystem or module 19 for use in inspecting a surface of a workpiece has a data acquisition system 54 that is connected by a communication network to a data reduction system 55. The data acquisition system 54 comprises a plurality of data acquisition nodes 570 (DANs 570), each of which is connected to and has associated therewith a collection and detection module 200 in the optical collection and detection subsystem 7.

The data reduction system 55 comprises a plurality of data reduction nodes 670 (DRNs 670). In the presently preferred yet merely illustrative embodiment, the data reduction system 55 comprises three DRNs 670 that have a combination of hardware and software that is operable to perform linear combining, digital filtering, threshold/haze calculation, and data collation and formatting. A system controller and processing unit 500 is connected to the data reduction system 55 via an interface or switch 660 arranged for a communication network or other system controller and processing unit 500 communication. The system controller and processing unit 500 outputs the data representative of the selected set of collectors to an analysis system 520.

The data acquisition system 54 is connected to the data reduction system 55 via an interface or switch 691, which could be any suitable communication system, such as an Ethernet™ communication system or, preferably, a Serial PCI compatible, switched interconnect communication system such as one based on the StarFabric™ open interconnect standard, "PICMG 2.17 CompactPCI StarFabric Specification" (ratified in May 2002).

Thus, multiple generic data recipients are available on a peer to peer basis to multiple sensors, essentially providing multiple computing destinations for output from the collection and detection assemblies 200. The signal processing described herein is described in greater detail in U.S. patent application Ser. No. 11/311,905, filed Dec. 17, 2005 and entitled SYSTEM AND METHOD FOR SIGNAL PROCESSING FOR A WORKPIECE SURFACE INSPECTION, which is hereby incorporated by reference, for background as if fully set forth herein.

Figure 4:
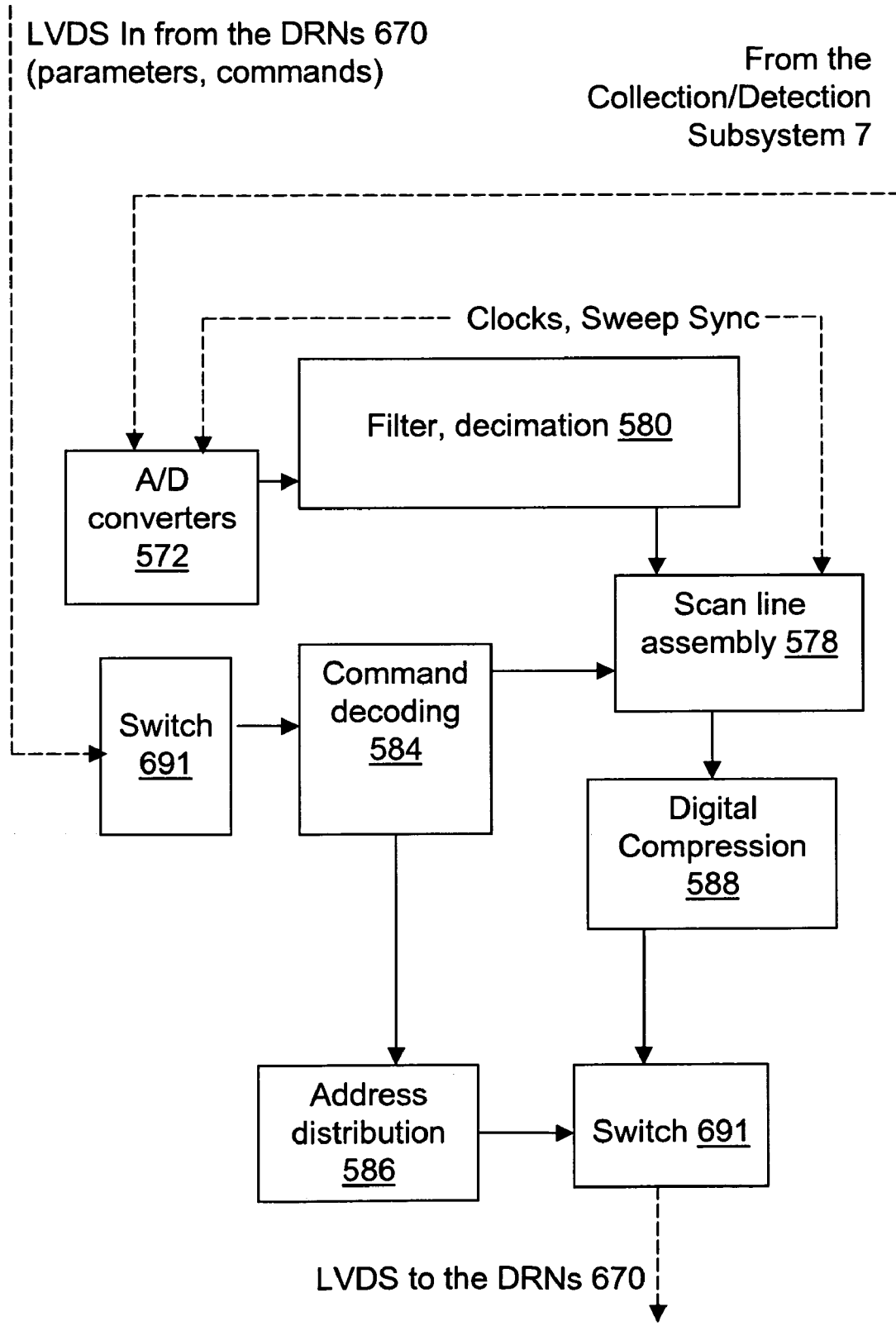
FIG. 4 is a functional illustration of the data flow in the Data Acquisition Nodes shown in FIG. 3.

Referring to FIGS. 4 and 5, a block diagram is shown that illustrates data flow in the surface inspection system 10. The optical collection and detection subsystem 7 provides voltage signals representative of the intensity of the scatter perceived by the multiple collectors in the optical collection and detection subsystem 7 to the plurality of data acquisition nodes (DANs) 570. In the system 10, the DANs 570 comprise a low noise receiver (not shown), filters and processing units (not shown), that as a unit are operable to perform anti-aliasing filtering, a software-configurable in-scan filtering, analog compression, A/D conversion, digital decompression of analog compression function, data decimation, and preparation of the data for transmission. In the preferred embodiment, the filters are a component of the processing unit, which comprises a digital signal processor and programmable logic such as field programmable gate arrays (FPGA).

The switch 691 to which the DANs 570 are connected to the DRNs 670 maps output associated with the collector/detector assemblies 200 to processor inputs in the DRNs 670. The DRNs 670 in system 10 comprise a master DRN and at least one slave DRN. The master DRN provides set up communications to the slave DRNs. DRN 670 are connected via a switch 660 to a system controller and processing unit 500, which comprises a combination of hardware and software that is operable to provide system control and monitoring, graphics user interface, and defect identification and sizing.

FIG. 4 is a block diagram showing data flow in the DANs 570 according to a preferred implementation of a method according to an aspect of the invention. As noted above, DANs 570 have a combination of hardware and software that is operable to perform digital filtering, and data collation and formatting. In the DANs 570, clock, sync and sweep signals are transmitted to the A/D converters 572 and the scan line assembly unit 578. Also as noted above, raw data is transmitted from the collector/detector assemblies 200 to the DANs 570. First arriving in the A/D converters 572, the digital data are then transmitted at a rate of 400 Mbytes/sec (for 2 channels, 4× oversampling) to a filter/decimation unit 580 for in-scan filtering and for decimation. The digital data are then transmitted at a rate of 100 Mbytes/sec to a scan line assembly unit 578.

Also as noted above, parameters and commands arrive at the DANs 570 at a low rate from the DRNs 670 via the StarFabric™ connection 691. The commands are decoded by a command decoding unit 584, which sends them to an address distribution unit 586 and scan line assembly unit 578.

The decoded commands control the scan line assembly unit 578 in assembling scan lines from the digital data. The assembled digital data are then transmitted at a rate of 80 Mbytes/sec to a digital compression unit 588 for data compression, and then transmitted out as low voltage data signals (also known as LVDSs) via the Serial PCI switch 691 to the DRNs 670. The address distribution unit 586 sends command signals to indicate the DRN destination of the newly compressed digital data.

FIG. 5 is a block diagram showing the data flow in the Data Reduction Nodes 670, which as described above, comprise a combination of hardware and software that is operable to perform linear combining, digital filtering, threshold/haze calculation, and data collation and formatting. The compressed digital data, which is assembled into scan lines, are transmitted at a rate of 80 Mbytes/sec (4 channel summing) to a data decompression unit 671. The data are decompressed at the data decompression unit 671 and then transmitted at a rate of 160 Mbytes/sec to a median filtering unit 672, and then to a data combining unit 673. Channels are created as described in U.S. patent application Ser. No. 11/311,925, entitled SYSTEM AND METHOD FOR INSPECTING A WORKPIECE SURFACE USING COMBINATIONS OF LIGHT COLLECTORS and filed 17 Dec. 2005, and hereby incorporated for reference, for background, as if fully set forth herein) and to DC Saturation logic 678.

The combined data are then transmitted at a rate of 40 Mbytes/sec (reduced to single channel) to a cross scan filtering unit 676 for cross-scan filtering to be performed on the data in accordance with the methods described in the U.S. Pat. No. 6,529,270, which is hereby incorporated by reference, for background if fully set forth herein.

The cross-scan filtered data are then transmitted to a noise/haze extraction unit 685 for calculation of statistical parameters of the filtered voltage signal data. The statistical parameters are then transmitted to the threshold calculation unit 686 for development of the threshold $T_{nm}$ to which the test voltage signals will be compared to identify defects. The threshold $T_{nm}$ is then transmitted to the thresholding unit 680, for use in the thresholding of the data from the cross scan filter unit 676. The thresholded data are then transmitted to the data collation and formatting unit 688. Noise/haze extraction, threshold calculation, and thresholding are described in greater detail herein.

The cross-scan filtered data are also transmitted to DC saturation logic unit 678, which operates to monitor the extent of saturation of photo-multiplier tubes ("PMTs") within the detector module 400. The results of the PMT 495 saturation monitoring are transmitted from the DC saturation logic 678 to the data collation and formatting unit 688, along with the line averaged data and thresholded data. If PMT saturation state is found, the scan currently being performed is aborted. If no PMT saturation state is found, the data are collated and formatted and transmitted at a rate of 500 Kbytes/sec to the system controller and processing unit 500.

Threshold Modification Process and Subsystem

General

FIG. 6a show an illustrative embodiment for a system and method for detecting a defect greater than a selected size, employing multiple threshold candidates and automated setting of the threshold from the multiple threshold candidates. In addition, the following illustrates a method and system according to another aspect of the invention for updating a constant false alarm rate threshold based on run-time data.

Threshold Selection Using Multiple Threshold Candidates

An improved system and method for defect detection in surface inspection systems comprises comparing a defect detection threshold against a test voltage signal associated with a test location on the surface of a workpiece to identify defects at the test location, where the defect detection threshold is selected from multiple threshold candidates. In one embodiment, the threshold candidates are developed using a plurality of threshold setting techniques. In another embodiment, the threshold is selected by adjusting the threshold automatically by the surface inspection system 10. In a further embodiment the threshold is adjusted in response to user inputs and estimates of selected components of the actual voltage signal derived from the actual voltage signal. Although a variety of threshold candidates may be used, in the illustrative embodiment, a first threshold candidate comprises a size-determined threshold candidate comprising a voltage that is representative of the smallest defect size that is detectable given the sensitivity of the surface inspection system 10. In the further embodiment, the size-determined threshold candidate comprises a constant sensitivity (CSENS) voltage.

In the illustrative embodiment, a second threshold candidate comprises a false alarm-based threshold that is representative of the smallest defect size that is detectable by the system 10 given the desired maximum acceptable probability of false identifications of a defect in the voltage signal output of the surface inspection system. The false alarm-based threshold may comprise a statistically-determined false alarm-based threshold be based on the maximum acceptable probability and run-time statistics of the voltage signals associated with an area of the workpiece surface under examination.

Statistically-Determined False Alarm-Based Thresholds

An improved system and method for defect detection in surface inspection systems comprises comparing a test voltage signal associated with a test location on the surface of a workpiece to identify defects at the test location against a statistically-determined false alarm-based threshold comprising a voltage based on statistics derived from voltage signals produced from scatter light intensity readings of the surface of the wafer. In another embodiment, the statistically-determined false alarm-based threshold comprises a threshold based on the statistics and a selected maximum acceptable probability of false identification of a defect in the voltage signal output of the surface inspection system. In another embodiment, the statistics comprise a component of the actual voltage signal attributable to haze (a haze component) and a component of the actual voltage signal attributable to noise (a noise component), and the estimates of the selected components are based on the actual voltage signal and accumulated run-time statistics.

The invention comprises a novel method to differentiate noise from particles, in which the threshold used to identify defects is based on statistical characteristics of current and historical voltage levels of readings of the scatter light intensity at locations on the surface of the workpiece:

Process for Threshold Modification

Figure 7:
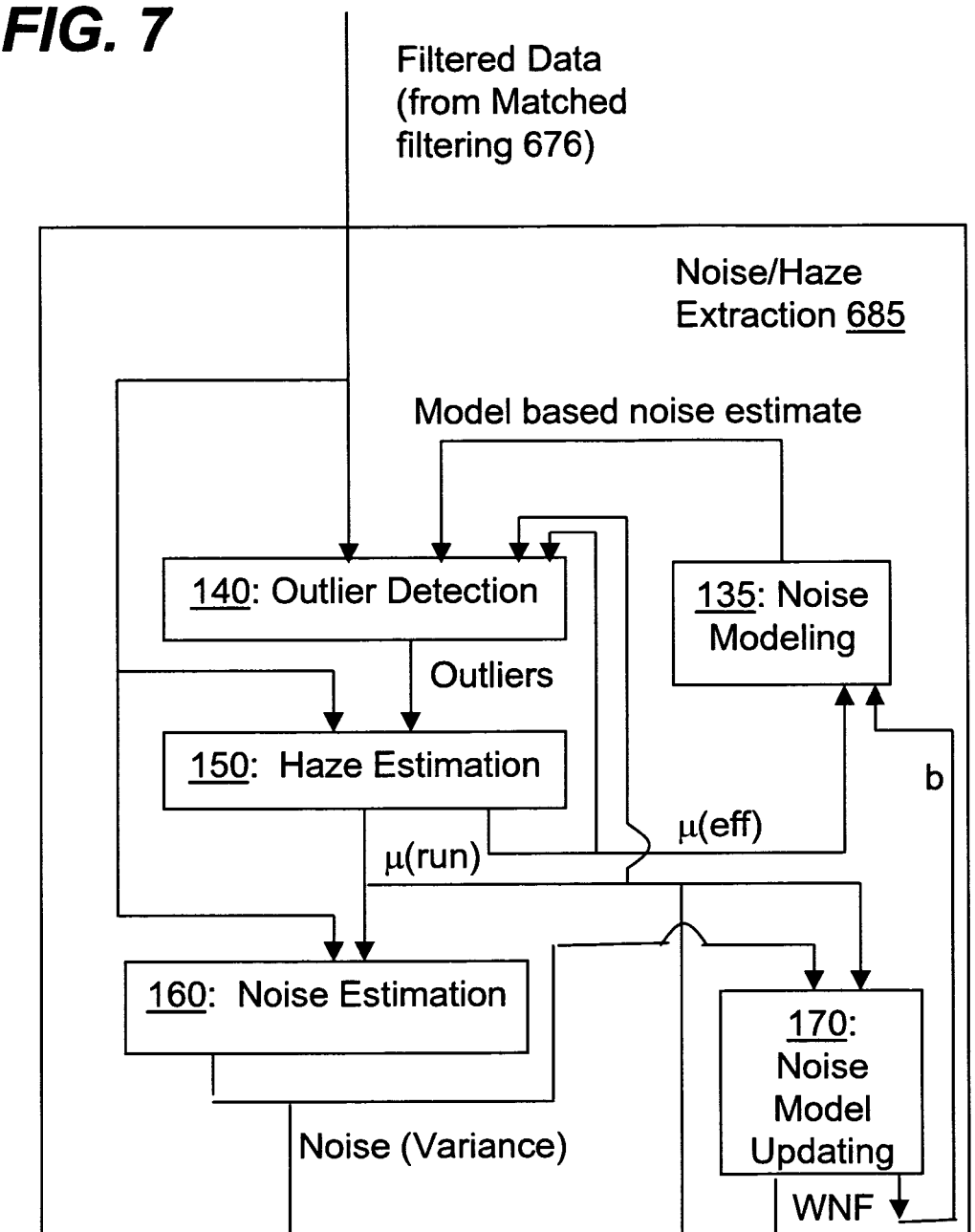
FIG. 7 is a functional illustration of the Noise/Haze Extraction unit 685 shown in FIG. 5.

A preferred process implementation 100 of threshold modification will now be described with reference to FIGS. 6-8. The process 100 for threshold modification starts with obtaining raw data from the optical collection and detection subsystem 7. The data is in the form of a data line comprising a vector of voltage values obtained from the photo-multiplier tubes ("PMT") in the detectors 400 of the optical collection and detection subsystem 7, based on intensity measurements of light scattered at locations on the surface of the workpiece along a selected scan line. For a scan line n of 400 scatter light intensity measurements, the $n^{th}$ data line is in the form of a vector $\vec{v}_n^{in}$:

$$\vec{v}_n^{in} = [v_{n0}^{in}, v_{n1}^{in}, \ldots v_{n399}^{in}]^T \quad (1)$$

with $v_{n0}^{in}$ being the voltage measurement that represents the scatter light intensity at the first of the 400 locations along the nth scan line; and T being the vector transpose operator.

Filtering Data

After obtaining the raw data, the process 100 then proceeds to filtering step 110, in which the input data is filtered. The filtering step 110 comprises both a median filtering step 112 and a matched filtering step 114.

The median filtering step 112 comprises trimming the tails of the probability distribution function (PDF) of the raw data from the PMTs in the detectors 400 of the optical collection and detection subsystem 7. It is known that PMT measurement noise has a Poisson probability distribution function (PDF). As PMT gain increases, the tails of the PDF grow larger. This growth causes detection of false counts for larger sizes. Median filtering eliminates the false counts due to PMT measurement noise by trimming the tails of the PDF.

A good example of the usefulness of median filtering is encountered in the wing collectors 210A, 210B in system 10. In the absence of a median filter, 48 nm PSL defects are detectable with 1e-9 false alarm rate, whereas this number drops down to 45 nm with the median filter.

The output of the median filtering step 110 is the vector $\vec{v}_n^{Med}$, which may be shown in the equation:

$$\vec{v}_n^{Med} = [v_{n0}^{Med}, v_{n1}^{Med}, \ldots v_{n399}^{Med}]^T \quad (2)$$

with $v_{nm}^{Med} = \text{Median}(v_{(n-1)m}^{in}, v_{nm}^{in}, v_{(n+1)m}^{in})$ being the median filtered voltage measurement at the $m^{th}$ location of the $n^{th}$ scan line.

The matched filtering step 114 comprises using the well-known matched filtering technique to provide filtering that is optimal for a desired result. Matched filtering is commonly used for obtaining measurements from systems having additive Gaussian noise. Matched filter detectors maximize the signal to noise ratio (SNR), which is essential to optimal detection. The output of the optical detectors is a voltage that represents the instantaneous optical power of the received light. The application of the two-dimensional matched filtering tends to decrease the peak values of the input voltage signals representing the instantaneous optical power. Accordingly, even when a saturated response is observed, the two-dimensional matched filtering tends to smooth the aggregate defect light intensity response. Matched filtering is described in detail in the U.S. Pat. No. 6,529,270, which is entitled APPARATUS AND METHOD FOR DETECTING DEFECTS IN THE SURFACE OF A WORKPIECE and which is hereby incorporated by reference, for background as if fully set forth herein.

Matched filtering is a 2-dimensional filtering process. In the system 10, the matched filtering step 114 is conducted using an in-scan filtering step 116 and a cross-scan filtering step 118. The filtering step 110 comprises performing in-scan filtering in the DAN 570 using the filter/decimation unit 580 (FIG. 4), then performing median filtering in the DRN 670 using the median filtering unit 672, and then performing cross-scan filtering in the DRN 670 using the cross-scan filtering unit 676. However, it is possible to conduct the filtering steps in an alternative order, such as conducting median filtering and matched filtering first in one dimension, and then conducting median filtering and matched filtering in the other dimension. Alternatively, median filtering could be conducted, followed by matched filtering first in one dimension, and then in the other dimension. Alternatively, 2-D median filtering could be conducted, followed by 2-D matched filtering.

The output of the in-scan filtering step 116 is a vector $\vec{v}_n^{IS}$ that may be shown in the equation:

$$\vec{v}_n^{IS} = [v_{n0}^{IS}, v_{n1}^{IS}, \ldots v_{n399}^{IS}]^T \text{ with } v_{nm}^{IS} = \sum_{j=-J}^{j=J} v_{xy}^{Med} F_{j+J}^{IS}, \quad (3)$$

where $x = n + \text{floor}((m - j)/400)$; $y = \text{modulus}(m - j + 400, 400)$;

and $F^{IS}$ is the in-scan filter of length $(2J + 1)$.

Note that in-scan filter requires voltages from the previous scan line to filter locations between 1 to J, and voltages from the next scan line to filter locations between (400-J) to 400.

The output of the cross-scan filtering step 118 is a vector $\vec{v}_n^{CS}$ that may be shown in the equation:

$$\vec{v}_n^{CS} = [v_{n0}^{CS}, v_{n1}^{CS}, \ldots v_{n399}^{CS}]^T \text{ with } v_{nm}^{CS} = \sum_{k=n-K}^{k=n+K} v_{km}^{IS} F_{k+K}^{CS}, \quad (4)$$

where $F^{CS}$ is the cross-scan filter of length $(2K+1)$.

Note that the cross-scan filter requires K past and K future scan lines.

Extracting Noise and Haze Components

After filtering the data, the process 100 then proceeds to the noise/haze component extraction step 120, in which the components of the actual voltage signal attributable to haze and noise are extracted from the voltage signal. The noise/haze component extraction step 120 comprises a feedback system, in which the outputs of previous iterations of the noise/haze component extraction step 120 are inputted back into the step 120 at the next iteration so that the components of the actual voltage signal attributable to haze and noise change in response to inputting the statistical characteristics of prior voltage signals.

The noise/haze component extraction step 120 in this preferred but merely illustrative process 100 is performed in DRN 670 using the noise/haze extraction unit 685. As shown in FIG. 7, the noise/haze extraction unit 685 has a noise modeling unit 135 for developing a noise model, an outlier detection unit 140 for detecting outliers that could represent defect events, a haze estimation unit 150 for estimating the haze component of the scatter light intensity signal, a noise estimation unit 160 for estimating the noise component of the scatter light intensity signal, and a noise model updating unit 170 for updating the noise model.

Outlier Detection

The outlier detection unit 140 determines whether the voltage level of the scatter light intensity reading at a selected location on the surface of the workpiece is different from a sufficient number of others in the set of data as to constitute a defect candidate. Outliers are data points representative of voltage signals corresponding to given locations on the surface of the workpiece that lie outside of the expected range of signal values, presuming that the signal represents a non-defect event. They may be positive of negative. Positive outliers are voltage levels of the scatter light intensity reading at a selected location on the surface of the workpiece that are significantly higher than those expected to be attributable to a non-defect event, such as haze. Negative outliers are voltage levels that are significantly lower than expected. They usually are the result of aberrant signals from the PMT, such as signals caused by collection of scatter light produced by defects of the surface outside of the surface area currently being scanned. Positive outliers and negative outliers are determined by thresholding, using the following calculations:

$$\text{Positive outlier} \Leftrightarrow v_{nm}^{CS} > \hat{\mu}_{(n-Q-1)m}^{run} + (\hat{\mu}_{(n-Q-1)}^{eff} - \hat{\mu}_{(n-2Q-1)}^{eff}) + \gamma_1 \hat{\sigma}_{n-Q-1}^{cc}$$

$$\text{Negative outlier} \Leftrightarrow v_{nm}^{CS} > \hat{\mu}_{(n-Q-1)m}^{run} + (\hat{\mu}_{(n-Q-1)}^{eff} - \hat{\mu}_{(n-2Q-1)}^{eff}) - \gamma_1 \hat{\sigma}_{n-Q-1}^{cc} \quad (5)$$

where $\gamma_1$ is the outlier threshold coefficient that marks all possible defect events and unlikely noise events, which typically occur less than 1% of the time, as outliers;

$v_{nm}^{CS}$ is the filtered data from the cross-scan filtering unit 676;

$\hat{\mu}_{(n-Q-1)m}^{run}$ is the run-time mean of the filtered data;

$\hat{\mu}^{eff}$ is the effective mean of the filtered data (both outputs from previous operations of the haze estimation unit 150, described below); and $\hat{\sigma}_{n-Q-1}^{cc}$ is the model-based noise estimate (which is output from the previous operation of the noise modeling unit 135, described below).

The inputs will be explained in further detail below, especially in reference to equations (6), (7), (8) and (9).

Figure 8A:
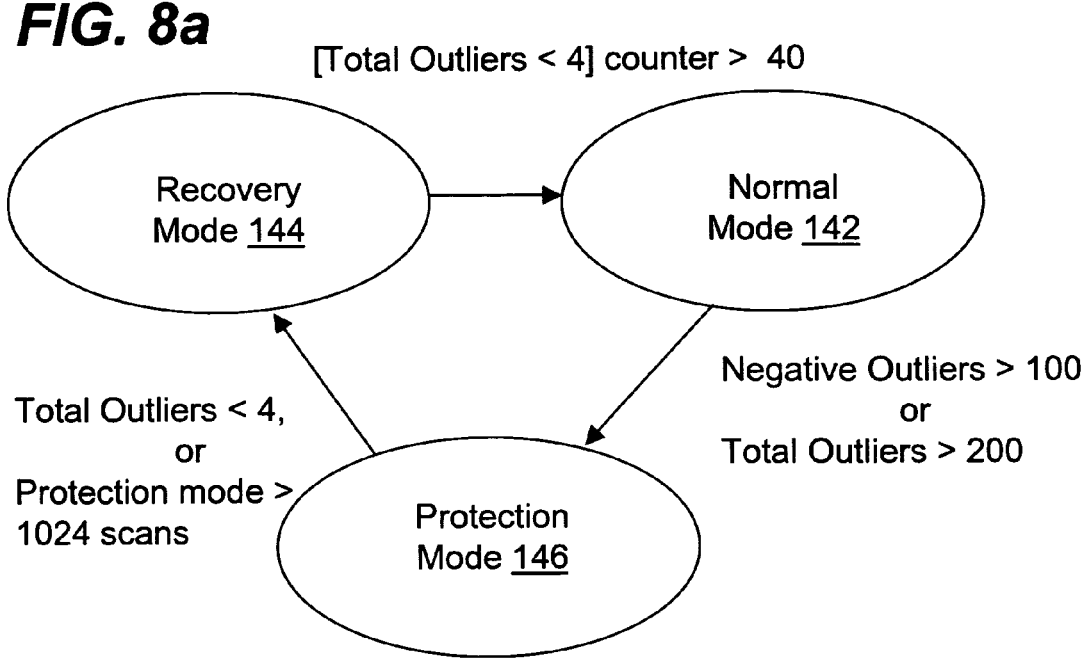

As shown in FIG. 8a, the output of the outlier detection unit 140 may be viewed as a state machine with three possible states: Normal mode 142, Recovery mode 144, and Protection mode 146. The initial state of operation is the Recovery mode 144. State transitions are controlled by the number of outliers and the number of scans in which the system has operated in a selected mode, as recorded in the state machine 688 associated with the noise/haze extraction unit 685.

The Normal mode 142 is entered from the Recovery mode 144 when fewer than four total outliers have been observed for forty consecutive scans. The Protection mode 146 is entered from the Normal mode 142 when more than 100 negative outliers have been observed, or when more than 200 total outliers have been observed. The Recovery mode 144 is entered from the Protection mode 146 when the number of observed total outliers then drops to fewer than four, or when there have been more than 1024 consecutive scans in the Protection mode 146.

Haze and Noise Defined

There are three distinct components to the scatter light that is collected and measured: defects, haze, and noise. The defect component is scatter light, usually of a high frequency, resulting from light scattered on surface anomalies that are introduced onto or into the wafer because of process deficiencies. Defects may be in the form of particles, scratches, or area spills.

The haze component is scatter light, usually of a low frequency, that is due to conditions such as Rayleigh scatter from the molecules of air near the surface of the workpiece and such as surface roughness of the workpiece. Rayleigh scatter is the scatter of light off the gas molecules of the atmosphere, principally nitrogen for ambient air. When surface inspection systems are operated in air, Rayleigh scatter is generated. This effect can be reduced by such means as operating in partial vacuum, use of a gas with lower scattering cross-section such as helium, etc. Because both of these methods for reducing Rayleigh scatter are difficult and expensive to implement, typically surface inspection systems are operated in air. Therefore, each collector in such systems typically will have a relatively constant background flux caused by Rayleigh scatter from the atmosphere.

Even though Rayleigh scatter is a relatively small scatter component compared to surface roughness scatter, it is usually more significant, especially in the back collector of a multi-collector surface inspection system such as system 10. In such systems, the surface scatter level is relatively low, for example, when wafer surfaces with an extremely good polish are inspected. (See "A Goniometric Optical Scatter Instrument for Bidirectional Reflectance Distribution Function Measurements with Out-of-Plane and Polarimetry Capabilities", Germer and Asmail, from "Scattering and Surface Roughness," Z.-H. Gu and A. A. Maradudin, Editors, Proc. SPIE 3131, 220-231 (1997)).

Finally, a measurement noise component is introduced by measurement system physical limitations. In system 10, the noise component is predominately shot noise, and it is equally distributed to all frequency components. "Shot noise" is the inherent, unavoidable noise associated with measuring photon flux. It is expected that shot noise will be present in any surface inspection system. When the collectors are operated in air, the shot noise in the output associated with P-polarized wing collectors tends to be dominated by Rayleigh scatter. The shot noise in the output associated with the back collectors tends to be dominated by surface roughness scatter.

Shot noise consists of random fluctuations of the signal in or from a photodetector that are caused by random fluctuations that occur in the detector or by fluctuations in the number of electrons (per second) arriving at the detector. The amplitude of shot noise increases as the average current flowing through the detector increases. The flux measurement is really counting a rate of how many photons per second are collected by the detector 400. The longer the period of counting, the more accurately one can measure the rate, other things being the same.

Haze Component Extraction (Mean Calculation):

In the haze estimation unit 150, the haze component of the scatter light intensity signal is extracted. This is accomplished by calculating the local area mean of the collected samples, excluding defects. It is generally desirable to average out the variation due to noise to provide the true background of the measurements, and use of the local mean can accomplish this.

The major challenge in extracting the haze component is to break the circular dependency between defects and noise. If a given high frequency variation is assumed to be noise, then it will be included in the haze and noise calculations, and consequently it will become noise.

The haze component is estimated according to this preferred process in a manner dictated by the mode identified in the outlier identification unit 140. For example, if the system is in Protection mode 146, all of the mean values are kept frozen in order to prevent the voltage levels associated with the large number of outliers from distorting the estimates of the haze component. If the system is in Recovery mode 144, the positive and negative outliers are replaced with their outlier thresholds, as shown in Equations (5), effectively clipping the outliers to their threshold values, and the following calculations are performed:

$$\hat{\mu}_{(n-Q)m}^{local} = \frac{1}{2Q+1} \sum_{i=n-2Q}^{n} v_{im}^{CS} \qquad (7)$$

$$\hat{\mu}_{(n-Q)m}^{run} = \frac{1}{2W+1} \sum_{i=m-W}^{m+W} \hat{\mu}_{(n-Q)i}^{local} \qquad (8)$$

$$\hat{\mu}_{(n-Q)}^{eff} = \frac{1}{400} \sum_{i=1}^{400} \hat{\mu}_{(n-Q)i}^{local} \qquad (9)$$

where $\mu_{(n-Q)m}^{local}$ is the mean value of the voltages that are averaged across consecutive scan lines;

$\hat{\mu}_{(n-Q)m}^{run}$ is the mean value of the voltages that are in the (2Q+1)×(2W+1) local area that is centered around the sample of interest; and $\hat{\mu}_{(n-Q)}^{eff}$ is the mean value of the voltages that are in the (2Q+1)×400 local area that is centered around the scan line of interest.

If the system is operating in Normal mode 142, the calculations of equations 7, 8, and 9 are also performed, but the positive and negative outliers are excluded from the inputs in order to prevent the voltage levels associated with the outliers from distorting the estimates of the haze component.

Outputs from the haze extraction unit 150 include the effective mean and the run-time mean. The effective mean, $\vec{\mu}_{(n-Q)}^{eff}$, comprises the average estimate of the component of the signal associated with haze for the filtered data from the cross-scan filtering unit 676. It is the average voltage level of the scatter light intensity readings in a selected local area, and is inputted into the outlier detection unit 140 and the noise modeling unit 135. The run-time mean, $\hat{\mu}_{(n-Q-1)m}^{run}$, comprises the mean for a sliding window of selected size of filtered data, and is input into the outlier detection unit 140, the noise model updating unit 170, and the threshold calculation unit 680 of the DRN 670.

Noise Component Extraction (Variance Calculation):

In the noise estimation unit 160 of the system 10, the noise component of the scatter light intensity signal is extracted. This is done by calculating variances of the collected voltage samples on a local area using the filtered data from the cross-scan filtering unit 676 and the run-time mean from the haze estimation unit 150. The noise component is also estimated according to this preferred process in a manner dictated by the mode identified in the outlier identification unit 140. For example, if the system is in Protection mode 146, variance values are kept frozen in order to prevent the voltage levels associated with the large number of outliers from distorting the estimates of the noise component. If the system is in Normal mode 142, the following calculations are performed on the filtered data from the cross-scan filtering-unit 676 (excluding the positive outliers and negative outliers in order to prevent the voltage levels associated with the outliers from distorting the estimates of the noise component).

$$(\hat{\sigma}_{(n-Q)m}^{local})^2 = \frac{1}{2Q+1} \sum_{i=n-2Q}^{n} (v_{im}^{CS} - \hat{\mu}_{im}^{run})^2 \qquad (10)$$

$$(\hat{\sigma}_{(n-Q)}^{eff})^2 = \frac{1}{400} \sum_{i=1}^{400} (\hat{\sigma}_{(n-Q)i}^{local})^2 \qquad (11)$$

where $\hat{\sigma}_{(n-Q)m}^{local}$ is the standard deviation value of the voltages that are averaged across consecutive scan lines; and $\hat{\sigma}_{(n-Q)}^{eff}$ is the standard deviation value of the voltages that are in the (2Q+1)×400 local area that is centered around the scan line of interest. The value Q may be different than the Q defined in mean calculation window.

If the system is in Recovery mode 144, the calculations of equations 10 and 11 are also performed on the filtered data from the cross-scan filtering unit 676 (also excluding the Positive Outliers and Negative Outliers), but the effective variance is overwritten by an artificially higher value, such as 25 times the effective variance, to protect from false counts.

The effective variance $\hat{\sigma}_{(n-Q)}^{eff}$ of the filtered data from the cross-scan filtering unit 676 is inputted into the noise model updating unit 170 for use in updating the noise model.

Noise Model Calculation

In order to distinguish noise from small particles, the preferred process implementation comprises a noise model that preferably is implemented using the noise modeling unit 135 to model the relationship between the haze and the noise variance. This model is intended to provide a gross approximation of noise variance. In the preferred implementation, the model is a quadratic relation. However, it is possible to develop other representations of the noise model.

An alternative noise model may take the form: $\sigma^2 = a + b\mu + c\mu^2$, which defines the "minimal" variance expected for given estimated level of haze, where a is dark noise term, b is shot noise term and c is wafer noise term (not necessarily from wafer speckle noise). In the preferred implementation, the terms a and c are set to zero, so that the noise model comprises the following calculation:

$$(\sigma_{n-Q-1}^{cc})^2 = b_{n-1} \cdot \mu_{(n-Q-1)}^{eff} \quad (6)$$

where $b_{n-1}$ is the shot noise term b from the previous operation of the noise/haze extraction unit 685.

The set of data with which the noise model is developed is selected in a manner such that the voltages are unlikely to be associated with a defect. If the data that are used to develop the noise model have voltage values that are associated with defects, the defect data would disrupt the accuracy of the noise model. Therefore, the set of data with which the noise model is developed is used to identify a non-defect window that comprises a range of scatter light intensity readings around a prior haze component estimate in which the reading is likely to represent a non-defect, including haze variations and noise, and excluding defects. The prior haze estimate comprises an estimate of the component of the voltage signals in an in-scan position that is attributable to haze, and the range is determined by a desired statistical or otherwise appropriate significance. The window of data used to develop the noise model may be described as having a size [(2W+1)(2Q+1)] that is centered on the sample of interest, where W and Q are pre-defined values identifying the desired size for the sliding window of data in the in-scan and cross-scan directions, respectively.

The noise model in the preferred but merely illustrative implementation has been developed using the effective mean from the haze estimation step unit and the shot noise term b from the noise model updating unit 170. The noise modeling unit 135 outputs the model-based noise estimate $\sigma_{CC}$, which is inputted into the outlier detection unit 140 for use in the next iteration of identifying outliers in the cross-scanned filtered data.

Noise Model Updating

In order for the noise/haze extraction unit 685 to maintain the accuracy of the run-time statistics used to develop the false alarm-based statistically determined threshold candidate, it is useful to update the noise model periodically, and preferably continually. Inputs into the noise model updating unit 170 for this purpose comprise the run-time mean from the haze estimation unit 150 and the effective noise variance from the noise estimation unit 160. This updating creates an updated term b, which, as noted above, is the shot noise term used in the noise model $\sigma^2 = a + b\mu + c\mu^2$.

The noise model preferably is updated only when the system is in the Normal mode 144. The term b can be updated using the following equation:

$$b_n = \frac{N-1}{N} b_{n-1} + \frac{1}{N} \left( \hat{\mu}_{(n-Q)}^{eff} / (\hat{\sigma}_{(n-Q)}^{eff})^2 \right) \quad (12)$$

where N is the number of scan lines accumulated during the scan;

The shot noise term b is inputted to the noise modeling unit 135 for use in developing an updated model-based noise estimate for use by the outlier detection unit 140 in the next iteration of identifying outliers in the cross-scanned filtered data.

The noise model updating unit 170 may be used in conjunction with a process or technique according to another aspect of the invention, in which the unit 170 is used to check the consistency of the surface inspection system 10. The process is referred to herein as the Workpiece Noise Factor WNF. Inputs into the noise model updating unit 170 for this purpose comprise the effective noise variance from the noise estimation unit 160 and the calibrated corrected standard deviation $\sigma_{n-Q-1}^{cc}$. The WNF is developed using the following equation:

$$WNF = (\hat{\sigma}(n-Q)^{eff})^2 / (\hat{\sigma}_{(n-Q)}^{cc})^2 \quad (13)$$

Under normal operating conditions, i.e., when the system 10 is operating according to its theoretical design, the WMF ratio is equal to one. The WNF ratio thus provides a measure of the extent of deviation from the normal or desired operation of the system 10. If the WNF value exceeds or becomes less than 1 by a selected amount, it may indicate that the scan data were not valid for some reason.

The WNF value for each scan line, along with other WNF related data, such as max, min, and average WNF, may be logged and inputted to the data collation and formatting unit 688 for processing and transmission to the system controller and processing unit 500.

The WNF data may be used by the system controller and processing unit 500 and/or the analysis system 520 to monitor the consistency of the surface inspection system 10. For example, scatter from an over-sized defect may be overwhelming the input scatter intensity readings to such an extent that the noise and haze statistics being calculated are no longer representative of noise or haze. Alternatively, intensity readings may be distorted due to irregularities in the shape of the edge of the wafer. Further, the WNF values may be used to identify aberrations that are neither surface defects nor surface roughness, so-called "hybridized" defects, which may not be detectable by conventional thresholding or by other inventive techniques described herein. One such hybridized defect comprises extensive and heavy surface roughness, also known as "speckle."

Figure 8B:
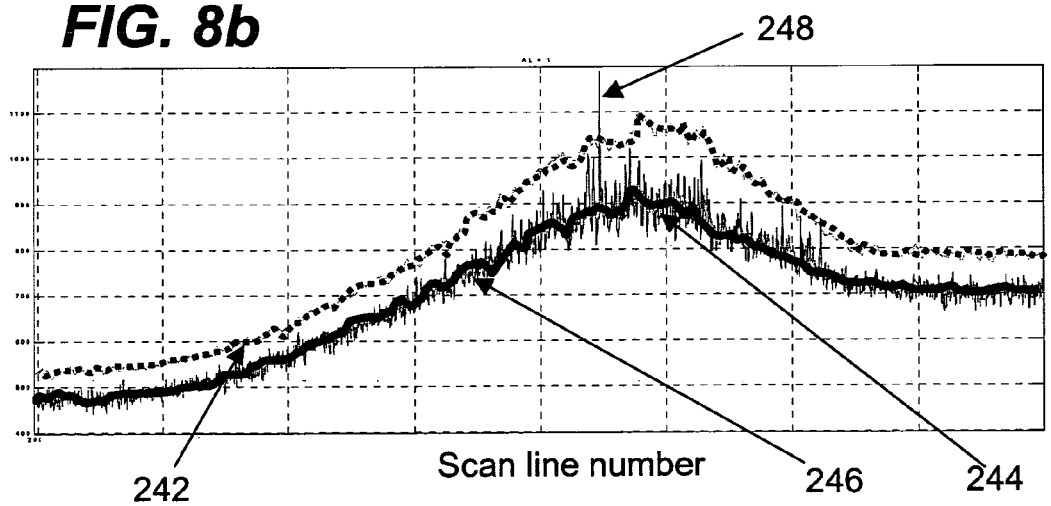
FIG. 8b is a graph of threshold values, mapped with data values and haze values over a selected number of scan lines.
Figure 8C:
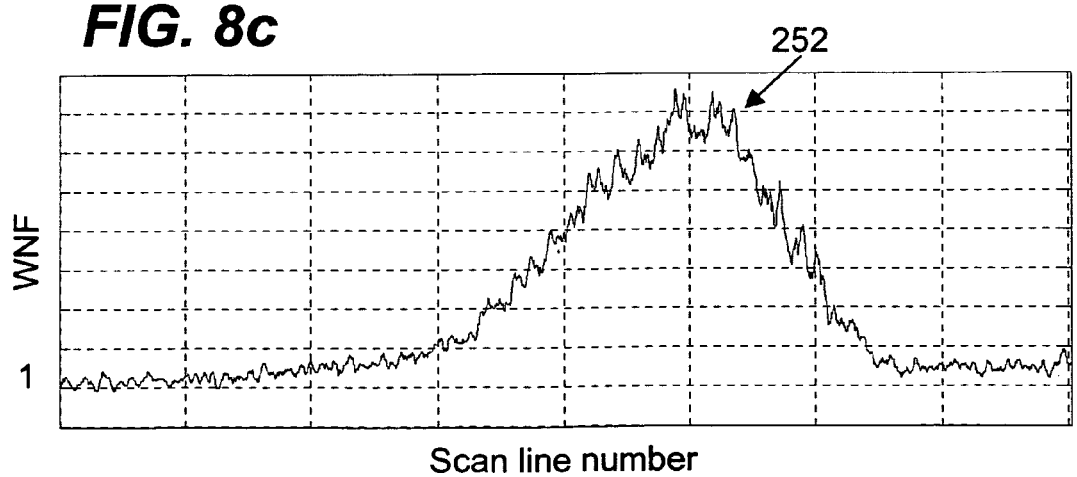
FIG. 8c is a graph of the Workpiece Noise Factor WNF, mapped over the same set of scan lines.

FIGS. 8*b* and 8*c* are graphs showing the use of WNF data to identify an hybridized defect. FIG. 8*b* is a graph of threshold values 242, mapped with data values 244 and haze values 246 over a selected number of scan lines. FIG. 8*c* is a graph of the WNF values 252 associated with the data values 244, mapped over the same set of scan lines. As can be seen in FIG. 8*b*, an over-threshold aberration 248 appears in the data values 244. It can be seen in FIG. 8*c* as well. WNF values 252 are high in the set of scan lines proximal to the scan line in which the aberration 248 appeared. The aberration 248 may result from the presence of a hybridized defect or from some other reason. The deviation of the WNF values 252 in the scan lines flag that further analysis should be undertaken.

When WNF values deviate from expected values such as in FIG. 8*c*, the system controller and processing unit 500 may elect to end the scan, to re-start the scan, or to reject the wafer as not o appropriate for scanning.

Threshold Calculation

When the noise PDF is known, it is possible to calculate a threshold with which to determine whether a voltage value represents a defect on the surface of a workpiece. The threshold is a voltage value that represents a scatter light intensity that may be expected to be representative of an actual defect.

In accordance with one aspect of the present invention, a threshold comprises a modifiable threshold that is selected from a plurality of threshold candidates. The threshold candidates may be developed using a plurality of threshold setting techniques, the inputs for which may comprise user inputs, the actual voltage signal, and estimates of selected components of the actual voltage signal.

In presently preferred embodiments and method implementations, a first threshold candidate comprises a size-determined threshold candidate which comprises a voltage that is representative of the smallest defect size that is detectable given the sensitivity of the surface inspection system. The size-determined threshold candidate may comprise a system sensitivity threshold based on a constant sensitivity (CSENS) voltage value. A user-specified system sensitivity threshold is based on the size of defects of interest, provided via binning definitions, as described herein further.

In another embodiment and method implementation, a second threshold candidate comprises a false alarm-based threshold candidate comprising a voltage that is representative of the maximum acceptable probability of false identifications of a defect in the voltage signal output of the surface inspection system. In a further embodiment, the false-alarm based threshold candidate comprises a statistically determined false-alarm based threshold candidate comprising a voltage based on run-time statistics of the voltage signals associated with an area of the workpiece surface under examination.

In a further embodiment and method implementation, the threshold $T_{nm}$ is determined to be the maximum of the size-determined threshold candidate and the false alarm-based threshold candidate, added to the run time mean $\hat{\mu}_{nm}^{run}$, according to the following equations:

$$T_{nm} = \max(k_0, \gamma \hat{\sigma}_n^{eff}) + \hat{\mu}_{nm}^{run} \quad (14)$$

with $k_0$ being a size-determined threshold value such as the CSENS value, $\gamma \hat{\sigma}_n^{eff}$ being a false alarm-based threshold value, which is developed from the noise (variance) $\hat{\sigma}_n^{eff}$ output from the noise/haze extraction unit 685; and $\gamma$ being the noise value in units of sigma $\sigma$ that is associated with the desired CFAR value.

The threshold calculation step 130 is conducted in the threshold calculating unit 686 as shown in FIG. 5. The output of the threshold calculation step 130 is the threshold $T_{nm}$, which is input into the thresholding unit 680.

Automatically Adjusted Channel-Specific Thresholds

In yet another preferred embodiment and preferred method implementation according to this aspect of the current invention, multiple threshold candidates are used in the identification of a defect or other characteristic of a workpiece surface. For example, in a surface inspection system such as system 10, scatter light is measured by multiple collection and detection modules 200, and is analyzed by channels that are formed from the modules 200. Channel formation is described in detail in U.S. patent application Ser. No. 11/311,925, entitled SYSTEM AND METHOD FOR INSPECTING A WORK-PIECE SURFACE USING COMBINATIONS OF LIGHT COLLECTORS and filed 17 Dec. 2005, hereby incorporated for reference, for background as if fully set forth herein.

In such systems, false alarms may be more likely in one channel than in another, or the sensitivity determined threshold voltage value may be different from channel to channel. In the past, users have monitored upper-bound haze limits or a series of capture rate scans to set thresholds for production wafers for each channel. Further, thresholds have been based on estimated noise levels. Using this aspect of the invention, during acquisition of workpiece data, local area noise levels are automatically measured for each channel, and detection limits are automatically established for each channel using these local area noise levels to obtain desired measurement confidence.

Therefore, the current invention allows for calculation of channel specific thresholds that are automatically changed in response to noise conditions.

Thresholding

After the threshold calculation step 130 (FIG. 6a), the process 100 proceeds to the thresholding step 180, which is conducted in the thresholding unit 680. In the thresholding step 180, the threshold $T_{nm}$ is compared to the cross-scanned filtered data from the cross-scan filtering unit 676 in order to determine whether or not a voltage value represents a defect on the surface of a workpiece, according to the following equation:

$$\text{defect} \Leftrightarrow \exists m: v_{nm}^{CS} > T_{nm} \quad (15)$$

Over-threshold events and haze and variance information are passed to the data collation and formatting unit 688 for transmission to the system controller and processing unit 500 and eventually the analysis system 520.

Multiple Threshold Tiers

In accordance with another embodiment and preferred method implementation according to this aspect of the current invention, multiple threshold tiers are provided for use in identifying characteristics of a workpiece surface. For example, the threshold level required to provide a desired level of confidence in identifying a particle on the surface may be different from the threshold level needed to identify scratches. This aspect of the current invention comprises the use by the surface inspection system of more than one tier of threshold. A first tier $T_1$ of thresholding, for example, is used to identify a first group of defect candidates and a second tier $T_2$ of thresholding is used to identify a second group of defect candidates.

Figure 9:
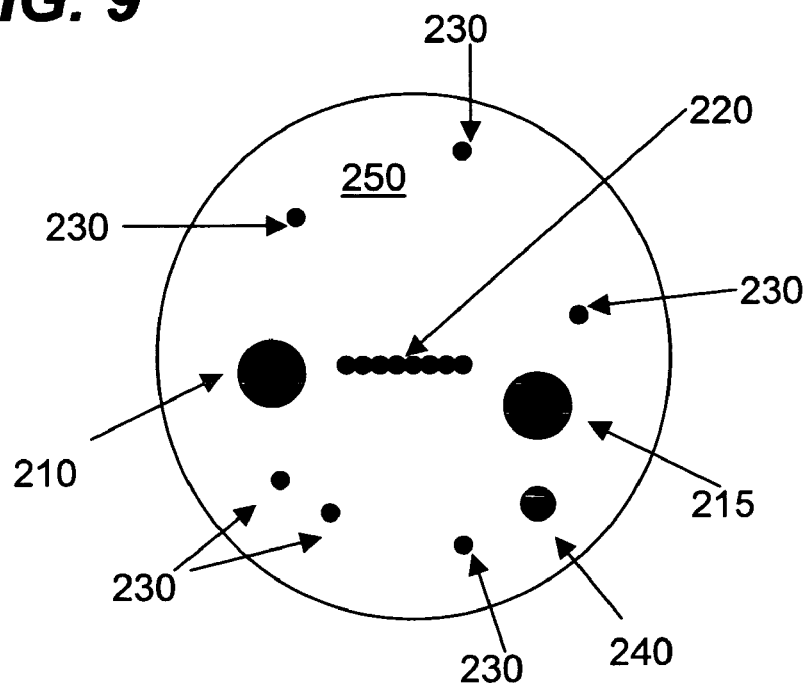
FIGS. 9 and 10 are top views of defect candidates on a surface 250 of a semiconductor wafer, based on thresholded voltages associated with scatter light intensity readings for a selected channel of a surface inspection system 10.
Figure 10:
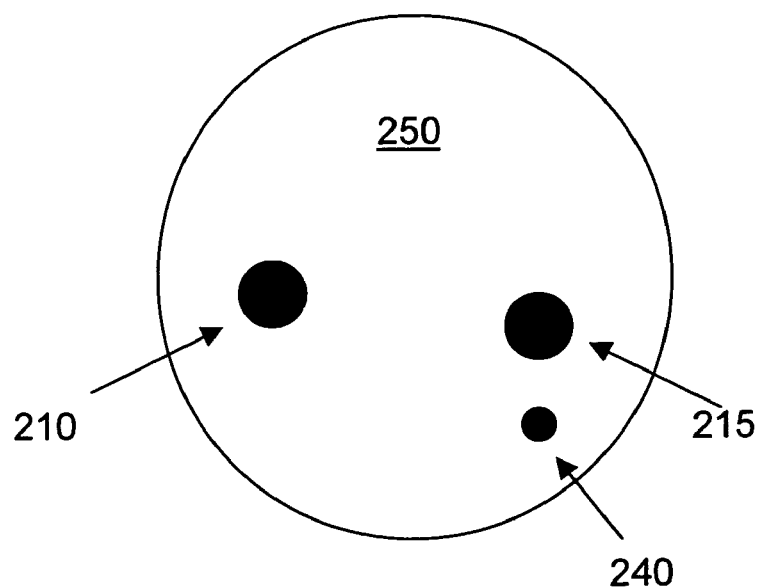

To illustrate these principles, FIGS. 9 and 10 are top views of defect candidates on a surface 250 of a semiconductor wafer, based-on-thresholded voltages associated with scatter light intensity readings for a selected channel of a surface inspection system 10. For purposes of this example, surface 250 has two point defects (particle 210 and pit 215), and a line defect (scratch 220). In FIG. 9, the intensity readings have been thresholded using a first threshold tier $T_1$. In FIG. 10, the intensity readings have been thresholded using a second threshold tier $T_2$.

In the preferred embodiment and preferred method implementation, the first threshold tier $T_1$ was created using a user-selected false alarm rate that exemplifies an acceptable level of false defect detection for the surface inspection system. The second threshold tier $T_2$ was created using a CFAR that exemplifies the maximum acceptable level of false defect detection for the surface inspection system. First tier thresholding in this instance comprises hardware validation of whether or not a defect candidate should be passed to the analysis system 520 for evaluation. Second tier thresholding here comprises a software threshold that validates inclusion of the defect candidate into a point defect bin, based on the haze level at the defect's location. Multiple tier thresholding in accordance with this aspect of the invention adjusts thresholds in order to maintain measurement confidence in the ability to correctly bin defects of a first type without sacrificing sensitivity required to identify defects of a second type. Thus, multiple tier thresholding in accordance with the present invention provides a system and method for selectable sensitivity and confidence levels in inspecting workpiece surfaces through adjustments in thresholds.

FIG. 9 shows the identification of candidates for all of the defect events (particle 210, pit 210 and scratch 220), along with several smaller sized candidates that are actually "false alarm" non-defect events 230, and a relatively larger sized candidate that constitutes "false alarm" non-defect event 240. FIG. 10, illustrating the defect candidates that were identified using a higher threshold, shows the identification of the defect events associated with the point defects and the relatively larger sized "false alarm" non-defect event 240. As can be seen in a comparison of FIGS. 9 and 10, use of a higher threshold level eliminated several "false alarm" non-defect events, but it also prevented identification of valid defect events such as scratch 220.

The data associated with the events identified using the first threshold are inputted into the system controller and processing unit 500 for analysis using a line defect identification algorithm, not shown. In the presently preferred embodiments and method implementations, only the data associated with the events identified using the second threshold are input into the system controller and processing unit 500 for analysis using the point defect identification algorithm.

Thus, thresholding at multiple tiers allows the surface inspection 10 to conduct surface characteristic identification using a plurality of inspection sensitivities. Using multiple threshold tiers, defects of one category (such as point defects) may be precisely identified without sacrificing the inspection sensitivity required for defects of a second category (such as line defects) to also be identified.

In multiple thresholding, each tier provides thresholding that is a factor of noise. In the preferred embodiment and preferred implementation, Tier 1, for example, runs at 5 sigma, or five times the statistically calculated noise level, while Tier 2 runs at 6.5 sigma, or six and one half times the statistically calculated noise level. The sigma coefficients are chosen based on the required confidence using known metrics, such the Cumulative False Count Rate (CFCR), which is determined by multiple scans of a wafer as defined in a Semiconductor Equipment and Materials Institute standard, specifically SEMI M50-1104—*Test Method for Determining Capture Rate and False Count Rate for Surface Scanning Inspection Systems by the Overlay Method* (© SEMI 2001, 2004).

Also in the preferred embodiment and preferred implementation, it is helpful to maintain constant the difference in voltage between the first tier and second tier thresholds, with the size-determined Tier 1 threshold value, $CSENS_{Tier1}$, derived according to the following equation, . . .

$$CSENS_{Tier1} = CSENS_{Tier2} - (CFAR_{Tier2} - CFAR_{Tier1})$$

where $CSENS_{Tier2}$ is the size-determined Tier 2 threshold value;

$CFAR_{Tier2}$ is the statistically-determined Tier 2 false alarm-based threshold value; and $CFAR_{Tier1}$ is the statistically-determined Tier 1 false alarm-based threshold value.

Thresholding States

In accordance with another preferred embodiment and preferred method implementation of this aspect of the current invention, multiple thresholding modes or tiers are used to accommodate user specifications. In this embodiment and preferred method implementation, the system 10 is provided with a thresholding modification system having three states of threshold selection: a size-determined threshold mode, a false alarm-based threshold mode, and a data responsive threshold mode.

If a user wants to exclude an event below a selected size, system 10 should be operated in the size-determined threshold mode, in which the size-determined threshold candidate (such as the CSENS value) is selected to be threshold $T_{nm}$.

If a user wants to identify all defects at a desired confidence level, the system 10 should be operated in the false alarm-based threshold mode, in which the false alarm-based threshold candidate, which is predetermined or developed based on the false alarm rate and the calculated noise variance, is selected to be threshold $T_{nm}$.

Finally, if a user wants to balance the ability of system 10 to identify defects with forecasted precision and its ability to sense defects, the system 10 should be operated in the data-responsive threshold mode, in which the threshold $T_{nm}$ is modified in response to changes in the scan data.

In the preferred embodiments and preferred method implementations, the surface inspection system 10 operates in a desired thresholding state in response to adjustments to the false alarm rate, which, as noted above, is an input to the development of the statistically-determined false alarm-based threshold. As shown in equation 14, the maxima of the size-determined threshold candidate and the statistically determined false alarm-based threshold candidate are selected as the threshold $T_{nm}$. When a sufficiently small false alarm rate is selected such that the size-determined threshold candidate will always be greater than the statistically determined false alarm-based threshold candidate, the size-determined threshold candidate will be selected as the threshold $T_{nm}$. The system 10 is said to be operating in the size-determined threshold mode.

When a sufficiently large false alarm rate is selected such that the statistically-determined false alarm-based threshold candidate is always greater than the size-determined threshold candidate, the statistically-determined false alarm-based threshold candidate is selected as the threshold $T_{nm}$. The system 10 is said to be operating in the false alarm-based threshold mode.

When the false alarm rate is selected such that the false alarm-based threshold candidate is occasionally greater than and occasionally less than the size-determined threshold candidate, the threshold $T_{nm}$ changes from time to time and the system 10 is said to be operating in the data-responsive threshold mode.

Figure 11A:
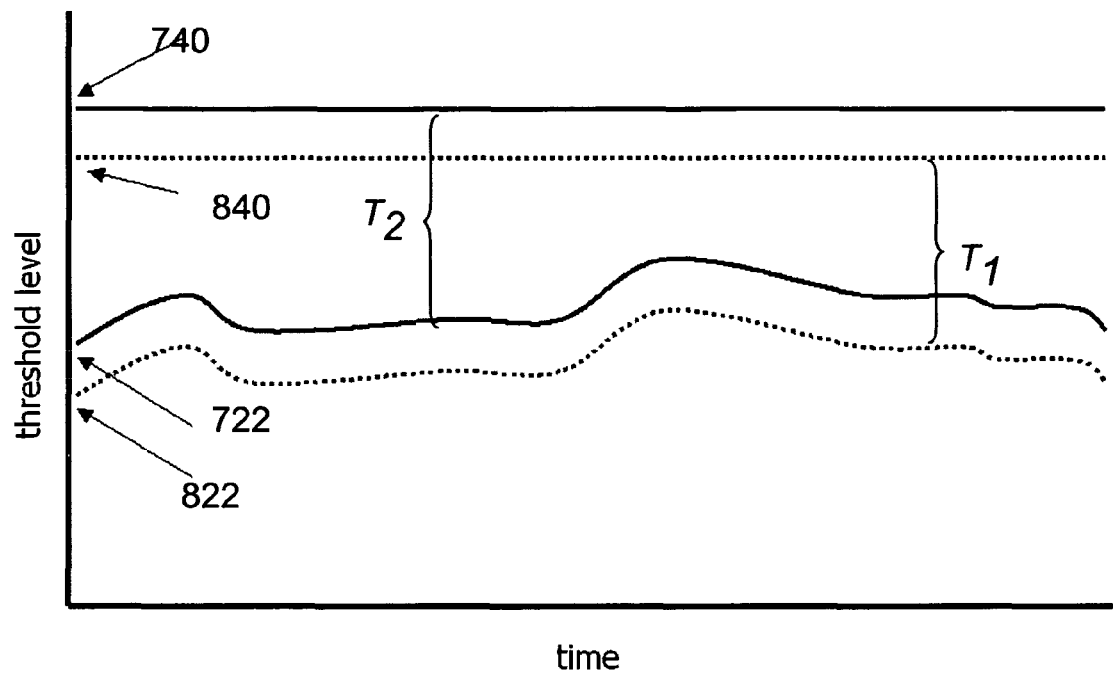
FIGS. 11a, 11b, and 11c are graphs showing multiple tier threshold calculation over time for a selected channel in a thresholding system embodying an aspect of the current invention.
Figure 11B:
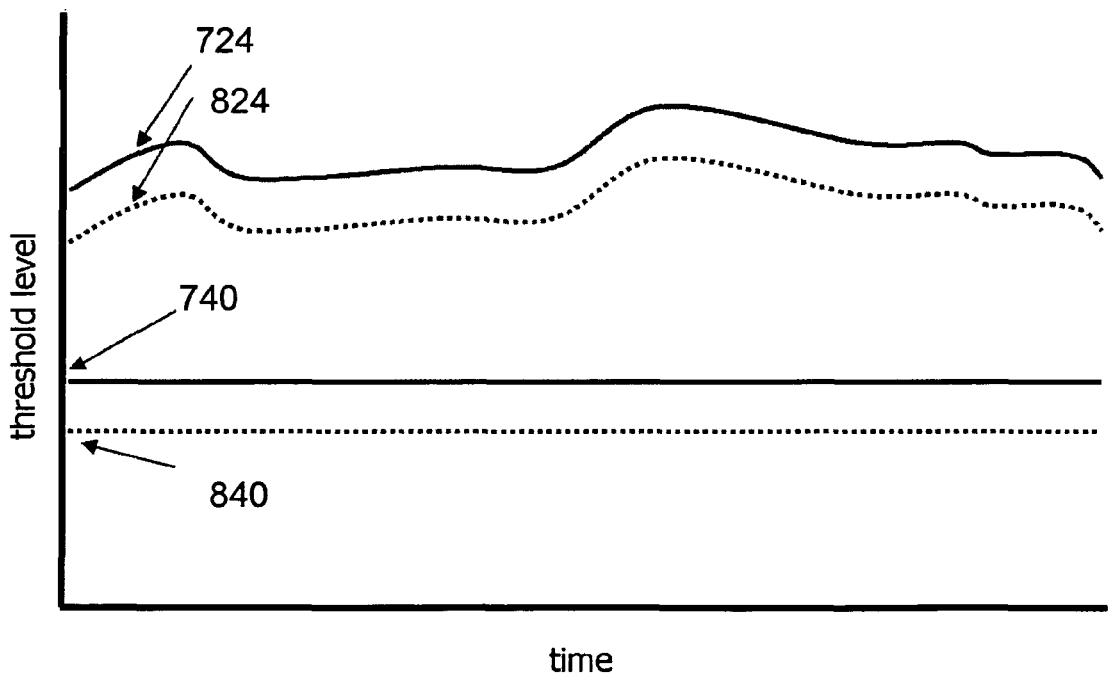
Figure 11C:
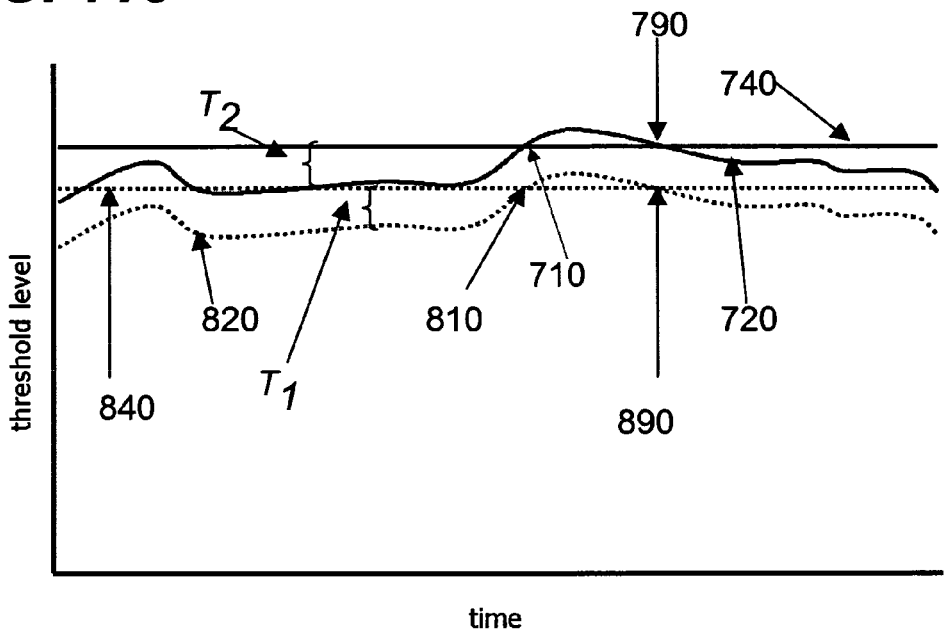

The graphs of FIGS. 11a, 11b, and 11c provide an illustrative multiple tier threshold calculation over time for a selected channel in a thresholding system embodying this aspect of the current invention. As noted, the thresholding system employs multiple tier thresholding and channel-specific thresholds, features described in detail herein above. FIGS. 11a, 11b, and 11c show threshold calculation in a thresholding system having two tiers of thresholds. A first tier $T_1$ may be used to identify a first characteristic category, such as line defect and false counts, and a second tier $T_2$ may be used to identify a second characteristic category, such as point defects and capture rate data.

FIG. 11a shows system 10 operating in the size-determined threshold mode. It includes first tier $T_1$ comprising first tier threshold candidates 822, 840 and a second tier $T_2$ comprising second tier threshold candidates 722, 740. The threshold candidates 822, 722 are the statistically determined false alarm-based thresholds based on the false alarm rate and noise variance, while the threshold candidates 840, 740 are the size-determined thresholds, based on the CSENS value. In the embodiment demonstrated in FIG. 11a, the false alarm rate is selected to be sufficiently small so that, for all times shown, the size-determined threshold candidates 840, 740 are greater than the statistically-determined false alarm-based threshold candidates 822, 722, respectively, and so the size-determined threshold candidates 840, 740, are selected as the threshold $T_{nm}$ for first tier thresholding and second tier thresholding, respectively.

FIG. 11b shows system 10 operating in the false alarm-based threshold mode. It includes first tier threshold candidates 824, 840 and second tier threshold candidates 724, 740. The threshold candidates 824, 724 are the statistically determined false alarm-based thresholds, while the threshold candidates 840, 740 are the size-determined thresholds. In the embodiment illustrated in FIG. 11b, the false alarm rate is selected to be sufficiently large so that, for all times shown, the size-determined threshold candidates 840, 740 are less than the statistically-determined false alarm-based threshold candidates 822, 722, respectively, and so the statistically-determined false alarm-based threshold candidates 840, 740 are selected as first and second tier thresholds $T_{nm}$, respectively.

FIG. 11c shows the system 10 operating in the data-responsive threshold mode. It includes first tier threshold candidates 820, 840 and second tier threshold candidates 720, 740. The threshold candidates 820, 720 are the statistically-determined false alarm-based thresholds, while the threshold candidates 840, 740 are the size-determined thresholds. In the embodiment illustrated in FIG. 11c, the false alarm rate is selected such that the statistically-determined false alarm-based threshold candidate is occasionally greater than and occasionally less than the size-determined threshold candidate, and so, for some of the times, the statistically-determined false alarm-based threshold candidate is selected as the threshold $T_{nm}$, and for other times, the size-determined threshold candidate is selected as the threshold $T_{nm}$.

In FIG. 11c, it can be seen that the first tier statistically-determined false alarm-based threshold candidate 820 is greater than the first tier size-determined threshold candidate 840 for the interval between time 810 and time 890, and at the other times, the first tier size-determined threshold candidate 840 is greater than the first tier statistically-determined false alarm-based threshold candidate 820. Therefore, using the threshold modification method according to this aspect of the current invention, as embodied in equation 14, the first tier threshold $T_{nm}$ (for identification of line defects and false counts) will be the first tier size-determined threshold candidate 840 until time 810, then the first tier statistically-determined false alarm-based threshold candidate 820 until time 890, and then the first tier size-determined threshold candidate 840 thereafter.

Similarly, it can be seen that the second tier statistically-determined false alarm-based threshold candidate 720 is greater than the second tier size-determined threshold candidate 740 for the interval between time 710 and time 790, and at the other times, the second tier size-determined threshold candidate 740 is greater than the second tier statistically-determined false alarm-based threshold candidate 720. Therefore, as embodied in equation 14, the second tier threshold $T_{nm}$ (for identification of point defects and capture rate data) will be the second tier size-determined threshold candidate 740 until time 710, then the second tier statistically-determined false alarm-based threshold candidate 720 until time 790, and then the second tier size-determined threshold candidate 740 thereafter.

FIG. 11c also reveals that the times of threshold modification (times 810, 710 and times 790, 890) are the same across tiers. This occurs because the statistically determined false alarm-based threshold candidates of different tiers are calculated using the same equation (equation 14) and are therefore only offset from each other by an amount determined by the difference between the false alarm rates used by the different tiers. In addition, the offset between the size-determined threshold candidates is a constant amount.

Therefore, despite the use of different thresholding tiers, threshold modification occurs at the same time for the preferred embodiment and preferred implementation of the thresholding modification system described herein. It should be noted that, in another embodiment, for example, in embodiments in which the statistically determined false alarm-based threshold candidates of different tiers are calculated using non-identical methods, the times of threshold modification would be different across tiers.

Thresholding State Modification

Figure 12:
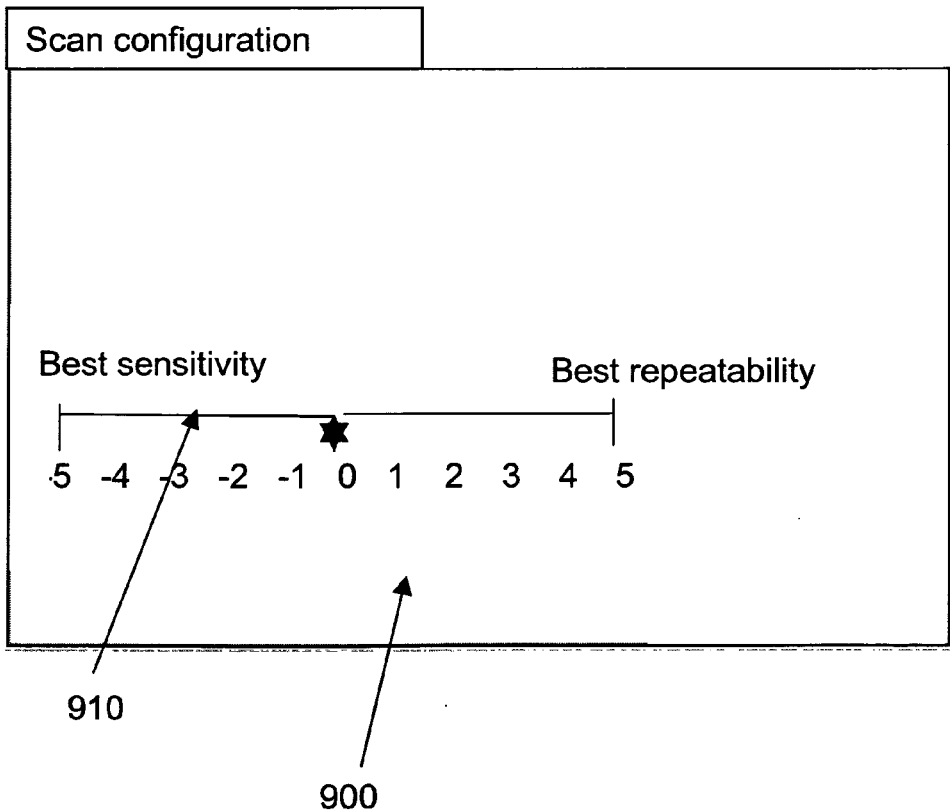
FIG. 12 is a diagram of a screen 900 in the graphics user interface of the surface inspection system shown in FIG. 1, showing a slider bar for use in user control of false alarm rate.

In the preferred embodiment and preferred method implementation, a user may control the thresholding state of the surface inspection system 10. In particular, a user may control the thresholding state of the surface inspection system 10 through the graphical user interface of the surface inspection system 10 by user-initiated adjustments to the constant false alarm rate that will be used to develop the statistically determined false alarm-based threshold candidate. Referring to FIG. 12, which is a diagram of a screen in the graphics user interface of the surface inspection system 10, a system user control of the false alarm rate of the current invention is shown. The graphical user interface of the surface inspection system 10 has a screen 900 for selecting configuration features for a scan of the surface of a wafer. Screen 900 has a slider bar 910 with which a user can select a desired level of system sensitivity for the system 10. Level markings on the slider bar 910 identify an extent of false alarm rate. In the preferred embodiment and preferred method implementation of the present invention according to this aspect of the invention, each marking represents an order of magnitude difference in the false alarm rate. The level of system sensitivity may be used to control the thresholding state of the surface inspection system 10. The slider bar setting in this embodiment applies to both thresholds by the same factor.

Figure 15:
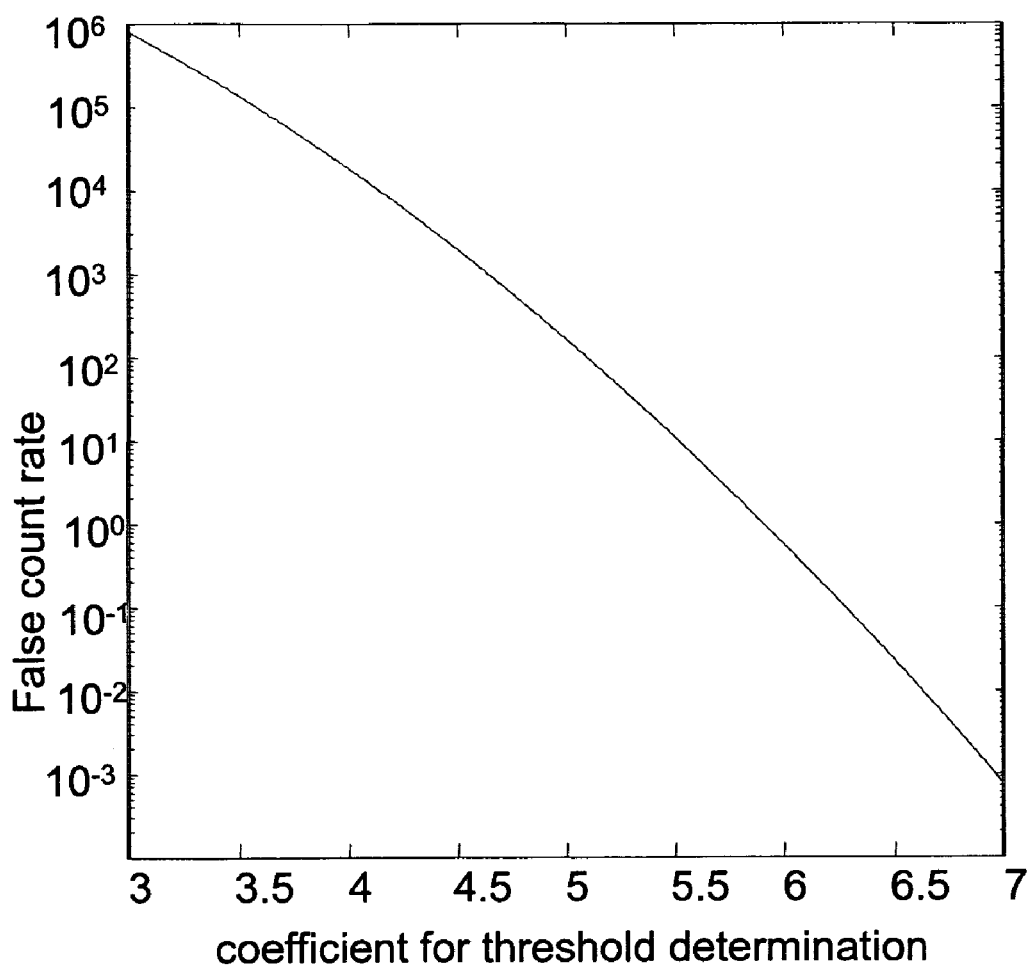
FIG. 15 shows the functional relationship in graphical form between expected false counts and the threshold normalized to sigma.

For example, positioning the slider bar 910 to the left would increase the level of sensitivity to detecting defect candidates. Increased sensitivity means that more defect candidates will be identified, but among the defect candidates will be more "false alarm" defect candidates. FIG. 15 shows the functional relationship in graphical form between expected false counts and the threshold normalized to sigma. As can be seen in FIG. 15, as the number of false counts decrease, the threshold normalized to the noise standard deviation increases. Therefore, positioning the slider bar 910 to the left selects a reduced value of $\gamma$.

If $\gamma$ is selected to be sufficiently low, it will force the value of the statistically-determined false alarm-based threshold candidate to always be lower than the size-determined threshold candidate, thus forcing the constant selection of the size-determined threshold candidate as the threshold $T_{nm}$, and thus automatically selecting the size-determined mode of inspection.

Similarly, positioning the slider bar 910 to the right will increase the level of repeatability of defect detections by driving down the number of false alarm defect candidates to be included in the identification results. (As noted above, repeatability of results usually comes at the expense of sensitivity of the system 10 to detecting all defect candidates). An increase in repeatability means a reduction in false alarms. Detecting a reduced number of "false alarm" defect candidates indicates an increase in $\gamma$. Therefore, positioning the slider bar 910 to the right selects an increased value of $\gamma$.

If $\gamma$ is selected to be sufficiently high, it will force the value of the statistically-determined false alarm-based threshold candidate to always be greater than the value of the size-determined threshold candidate, thus forcing the constant selection of the false alarm-based threshold candidate as the threshold $T_{nm}$, and thus automatically selecting the false alarm-based mode of inspection.

Positioning the slider bar at a point between the ends of the slider bar would provide the system with a balance between the ability of system 10 to identify defects with precision and its ability to sense defects. A moderate value of $\gamma$ will balance system sensitivity and results repeatability. Positioning the slider bar 910 in a middle area will result in a false-alarm-rate such that the statistically-determined false alarm-based threshold candidate is occasionally greater than and occasionally less than the size-determined threshold candidate, and so, for some of the times, the statistically-determined false alarm-based threshold candidate is selected as the threshold $T_{nm}$, and for other times, the size-determined threshold candidate is selected as the threshold $T_{nm}$. Therefore, the system 10 will be operating in the data-responsive threshold mode. The ratio of time that the statistically-determined false alarm-based threshold candidate as opposed to the size-determined threshold candidate is selected as the threshold $T_{nm}$ will depend on the location the user selects to position the cursor of the slider position bar 910.

Minimum Sort Size

When defect events are identified during analysis of a workpiece surface, they are also categorized by characteristics such as size. The defined specification for the categorization is known as a recipe, and the categorization itself is known as a binning configuration, with the defect events sorted into bins using the configuration defined by the recipe. Further, the sorting process itself is often known as grading the workpiece.

In accordance with another preferred embodiment and preferred method implementation according to this aspect of the present invention, a system and method are provided for assessing the capability of a multi-channel surface inspection system to analyze a workpiece to selected defect size identification specifications. This embodiment and method implementation comprises comparing channel-specific statistically determined false alarm-based threshold values for a portion of the workpiece to a specified minimum defect size, and finding the surface inspection system suitable to analyze the workpiece if the specified minimum defect size exceeds a selected number of the channel-specific statistically determined false alarm-based threshold values. In a further embodiment, finding the surface inspection system to be suitable comprises finding the surface inspection system to be suitable if the specified minimum defect size exceeds at least one of the channel-specific statistically determined false alarm-based threshold values. A further embodiment comprises comparing channel-specific statistically determined false alarm-based threshold values for a portion of the workpiece to associated channel-specific specified minimum defect sizes, where a minimum defect size is provided for each channel.

In accordance with this aspect of the invention, a workpiece may be determined to be capable of being graded if a selected number of channel of a multi-channel surface inspection system will support the sort requirement defined in the binning configuration for a wafer, the minimum sort size found in the defect binning determining the user's desired sort size. In the preferred embodiment and preferred implementation of the current invention, the present invention contemplates passing the wafer if at least one channel will support the sort requirement defined in the binning configuration at any given location on the wafer, the minimum sort size found in the defect binning determining the user's desired sort size.

The minimum sort size is defined to be the minimum required defect size that a system 10 must be capable of detecting on the surface of a workpiece in order to meet the review specifications for the workpiece under inspection. In semiconductor manufacturing, different processes require workpieces to meet different requirements. If a workpiece such as a semiconductor wafer is intended for a specific application that requires the identification and sizing of defects of at least a selected size (minimum sort size) on the workpiece, a surface inspection system that cannot identify defects of the minimum sort size cannot grade the wafer to the required specification. The requirements of the process will define the specifications for acceptance of the workpiece for use with desired production process.

The inability to identify a defect having a size larger than the minimum sort size is often due to excessive haze in the region above the workpiece, so it can be said that the wafer is rejected for haze. In the past, users needed to manually input the required sort sizes to be used in the defect sorting algorithm for each channel and the largest allowable haze values that would support the measurement and sorting process. The manual management of collectors and channels was workable in prior art systems because the number of channels and collectors was limited. The complexity of a multi-channel, multi-collector surface inspection system such as system 10 renders the manual management of the collectors and channels extremely difficult and time-consuming.

Figure 13A:
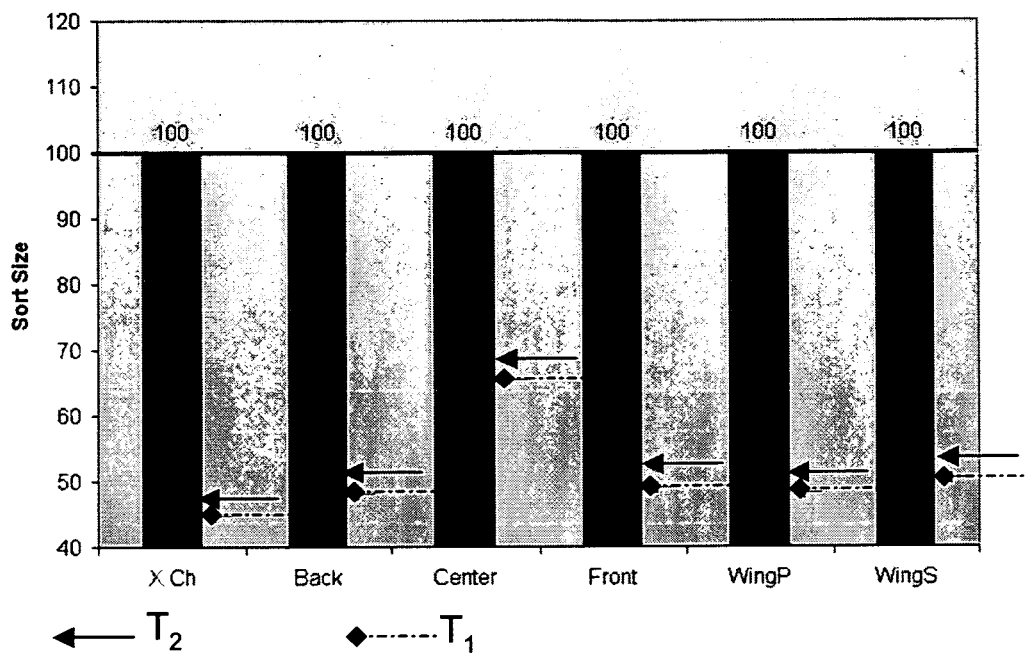
FIGS. 13a, 13b, and 13c are bar graphs of the threshold candidates and sort sizes for defined channels of a multi-channel surface inspection system 10.

In accordance with this aspect of the current invention, minimum sort size is determined in accordance with the above description of automatic thresholding, with the minimum sort sizing comprising the size-determined threshold value described above. Referring to FIG. 13a, a bar graph of the threshold candidates and sort sizes is shown for defined channels of a multi-channel surface inspection system 10, and specifically the X, back, center, front, P-polarized wing, and S-polarized wing channels. FIG. 13a also shows the statistically-determined false alarm-based threshold values $T_1$, $T_2$, and size-determined threshold for each defined channel. As noted above, the minimum sort size, or the size-determined threshold voltage value, is the minimum size of defect that must be detectable by the system 10 in order for the binning to support the specifications of the application for which the defect is intended. The minimum sort size, which can be seen to be 100 nm, is the same for all channels, but, as noted above, the threshold voltage values $T_1$, $T_2$ vary by channel. It can be seen in FIG. 13a, that the voltage values $T_1$, $T_2$ are less than the size-determined threshold voltage value in each channel, so it can be said that the system 10 will support the minimum sort requirement for the workpiece and its intended application, and the wafer can be found to be capable of being graded.

Figure 13B:
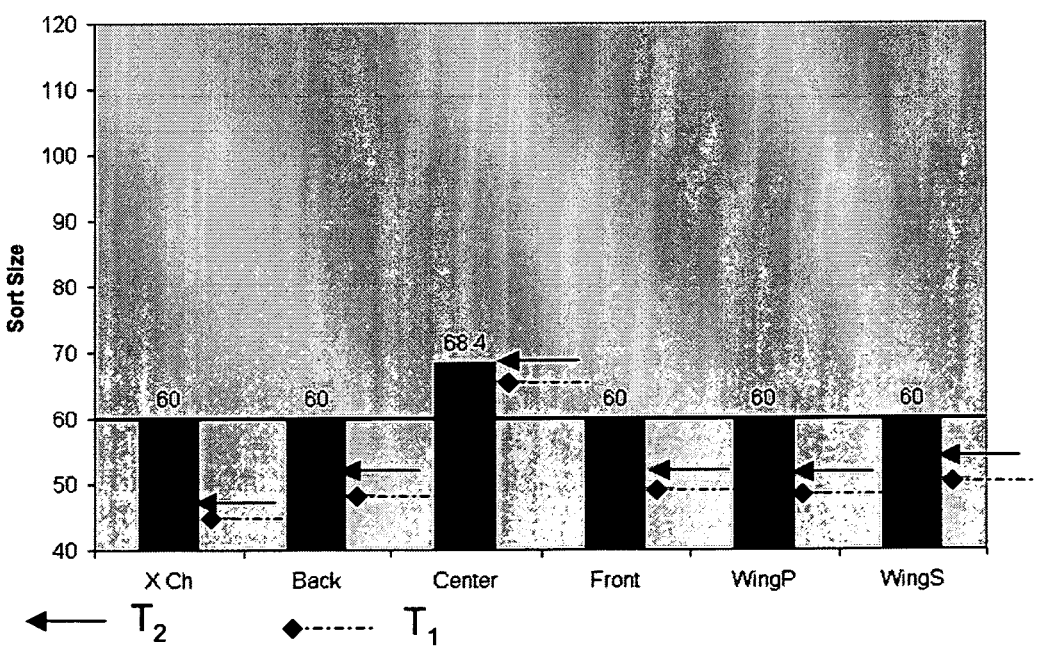

FIG. 13b shows a bar graph of the sort sizes, in which the minimum sort size is increased to 60 nm. It can be seen that, for all channels except the center channel, the threshold voltage values $T_1$, $T_2$ are less than the size-determined threshold voltage value. The center channel will not support the minimum sort requirement for the workpiece and its intended application. However, since the other channels will support the minimum sort requirement for the workpiece and its intended application, the workpiece can be found to be capable of being graded.

Figures 13C, 14:
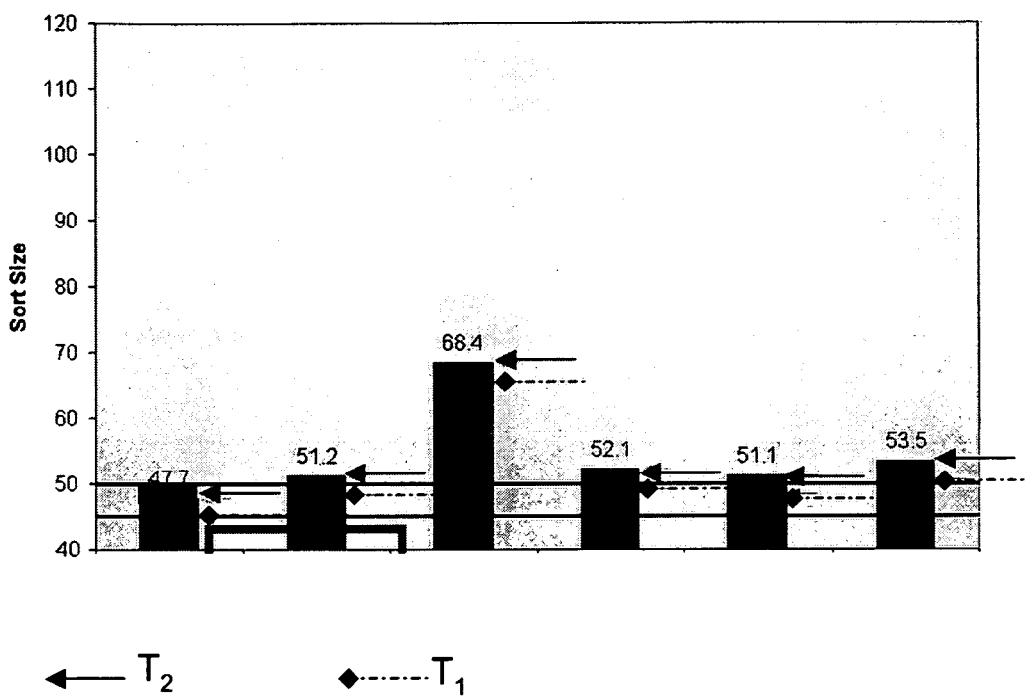
FIG. 14 presents a display of the bin counts for defects found on a workpiece, organized by defect size bins.

FIG. 13c shows a bar graph of the sort sizes, in which the minimum sort size is reduced to 50 nm. It can be seen that, for all channels except the X-channel, the threshold voltage values $T_1$, $T_2$ are greater than the size-determined threshold voltage value. None of the channels except the X-channel will support the minimum sort requirement for the workpiece and its intended application.

System design choice can be used to determine how many channels need to meet the minimum sort size requirement for the workpiece and its intended application in order for the workpiece to be found to be capable of being graded. In the preferred embodiment and preferred method implementation, only one channel needs to meet the minimum sort requirement, so the workpiece, having thresholds shown in FIG. 13c, also would be found to be capable of being graded.

Operation

To illustrate the operation of the preferred embodiment and preferred method implementation according to this aspect of the current invention, the minimum sort size is selected by the user based on the expected quality of the wafer. If the user fails to enter a required minimum sort size, the Default Minimum Sort Size setting is zero. A zero value indicates that the minimum bin size will be used to validate the scan results. The system will post a flag in the flaw map display that validates the scan results against the minimum size defined in the flaw bins, e.g. if the first bin starts at 60 nm then the system will test that at least one channel allows sorting at 60 nm.

If all channels exceed the minimum sort size requirement, the wafer is rejected for haze. A user could still choose to continue the wafer scan, because the automatic adjustment of thresholding using statistically-determined false alarm-based thresholds as described above maintains a level of measurement confidence. However, it is helpful if the data associated with a wafer scan that failed to meet minimum sorting requirements is tagged accordingly. A display for the bins containing data that failed to meet the minimum sorting requirements could be highlighted a different color, e.g., colored yellow, and its text could be displayed in another color.

In the graphics user interface for the system 10, the composite defect bin range will be highlighted as a failure if the minimum size for the bin has been exceeded. For example, FIG. 14 presents a display of the bin counts for defects found on a workpiece, organized by defect size bins. The display of FIG. 14 shows the size data for defects sorted into a composite bin, in which the bin counts for all channels have been combined into one bin.

The display in FIG. 14 illustrates a sorting recipe in which sorting ranges in size from 0.050 microns (50 nm) to greater than 1 micron. It can be seen that bin 1 contains the defect size that comprises the minimum sort size of 50 nm. If the statistically-determined false alarm-based threshold for all channels exceeds 50 nm, the wafer is rejected for haze. If the statistically-determined false alarm-based threshold for at least one of the channels is lower than 0.060 nm, the minimum sort size for bin 2, it is only the defects in bin 1 that failed to meet the meet minimum sorting requirements. The scanning may continue and all or part of the display row for bin 1, the bin that could be highlighted a different color, e.g. colored yellow, and its text could be displayed in another color.

In the preferred embodiment and preferred method implementation, a user can define the bins to be included in workpiece grading, thus effectively selectively enabling and disabling bins. If no channel allows sorting at a defect size that is lower than a bin's minimum defect size, the user could disable the bin for grading purposes but still keep track of the defect count in the bin, for example, for process variation monitoring. The disabled bins could be highlighted, using a different color, e.g. yellow, but, since the failure to sort at the minimum bin defect size was not required according to the desired recipe, its actual status as a sorting non-failure could be demonstrated by displaying the text in the same color as the other text (i.e., black).

If the minimum sort size for the bin has been exceeded for one or more channels, but not all channels, the display, or portions of the display and the user prefer to continue binning defects below the sort requirements, for example, to intercept excursions that reduce yield, the bins should be highlighted, but not as failures, using a different color, e.g. orange.

Setup Time:

Thresholds, noise and haze estimates, and noise models are provided based on current and historical data. At system start up, the historical data is not available. Therefore, the following conditions are selected for start up conditions. In the outlier detection unit 140, the effective mean $\mu_{eff}$, used as an input, is defined to be zero. In addition, recalling that the effective means $\mu_{eff}$ is the history based haze estimate for the filtered data, developed using data from a selected number of previous operations of the haze estimation unit 150, and recognizing that at set-up there are no previous operations of the haze estimation unit 150, the delay associated with the effective means, is selected to be zero at start up. The delay increases by 1 during each subsequent operation of unit 140 until the selected number of previous operations of the haze estimation unit 150 has been reached.

At set-up, a value is selected for the variable b to be large enough to force most events to not be an outlier. It is chosen by experimentation during system development. Also at set-up, the model based noise estimate $\sigma_{CC}$ is selected to be an empirically determined seed value based on previous measurements or theoretical analysis. Finally, the Recovery mode 142 is selected as the initial state for purposes of system operation.

Threshold Modification Using Threshold Offsets

It should be noted that the system and method for detecting a defect greater than a selected size, employing multiple thresholding candidates and automated setting of the threshold from the multiple threshold candidates, can be implemented in several different ways. For example, in a further embodiment, an improved system and method for defect detection comprises developing the threshold based on one of multiple threshold offset candidates. In one embodiment, the threshold offset candidates are developed using a plurality of threshold offset setting techniques. In another embodiment, the threshold is developed by adding a selected threshold offset candidate to an average value of the haze component of at least a subset of the actual voltage signal output of the surface inspection system. At least one of the selected threshold offset candidates may be adjusted automatically by a surface inspection system in response to statistical characteristics of the voltage signals. In a further embodiment, the threshold offset candidate is adjusted in response to user inputs and estimates of selected components of the actual voltage signal.

Although a variety of threshold offset candidates may be used, in one embodiment, a first threshold offset candidate would comprises a size-determined threshold offset candidate, which comprises a voltage that, when added to the an average value of the haze component of at least a subset of the actual voltage signal output of the surface inspection system, would be representative of the smallest defect size that is detectable given the sensitivity of the surface inspection system. The size-determined threshold candidate could comprise a constant sensitivity (CSENS) offset voltage value.

In one embodiment, a second threshold offset candidate could comprise a false alarm-based threshold offset candidate comprising a voltage that, when added to the an average value of the haze component of at least a subset of the actual voltage signal output of the surface inspection system, is representative of the maximum acceptable probability of false identifications of a defect in the voltage signal output of the surface inspection system. In a further embodiment, the false alarm-based threshold offset candidate comprises a statistically determined false-alarm based threshold candidate comprising a voltage based on run-time statistics derived from the voltage signals associated with an area of the workpiece surface under examination.

In the implementation of the process of threshold modification involving threshold offset candidates, the process 102 is shown in FIG. 6b. The process 102 starts with obtaining raw data from the optical collection and detection subsystem 7. After obtaining the raw data, the process 102 then proceeds to the same filtering step 110 as in the process 100. When the data is filtered, the process 102 then proceeds to the same noise/haze component extraction step 120 as in process 100. The process 102 would then proceed to a threshold offset calculation step 132 for calculation of the threshold offset candidates and selection of the desired threshold offset. In one implementation, the desired threshold offset comprises the maximum of a size-determined threshold offset and a false alarm-based threshold offset, preferably a statistically determined false alarm-based threshold offset. The process 102 would then proceed to a threshold calculation and thresholding step 182 for calculation of the threshold from the desired threshold offset and the average value of the haze component of at least a subset of the actual voltage signal output of the surface inspection system.

CONCLUSION

From the foregoing, it can be seen that various aspects of this invention provide thresholding based on both user selected and statistically determined conditions. Thresholds that satisfy both defect identification precision and system sensitivity criteria may be used for calculation. Aspects of the invention allow the user to set the thresholds based on the data and based on inspection system size sensitivity simultaneously. The methods permit calculation and quantification of the amount of noise during data collection and setting of the thresholds based on the statistics of the noise to yield a false alarm rate that is determined by the user as well as a user requested minimum defect size. It is very useful for semiconductor wafer manufacturers because: 1) the method provides confidence that the detected defects are indeed real; 2) the method alerts the user in cases where a prescribed defect size is not detectable; 3) the method employs the measurement system as efficiently as possible; 4) the method minimizes the setup time for a new type/batch of wafer on the production floor; and 5) the method does not flood the measurements with unnecessary data when the user is not looking for optimal sensitivity.

The invention has been described in terms of it use in the analysis of unpatterned wafers. However, it is to be understood that the invention is not limited to use in the analysis of wafers. The invention could be applied to the analysis of any suitable workpiece, such as glass and polished metallic surfaces and film wafers.

Additional advantages and modifications will readily occur to those skilled in the art. Therefore, the invention in its broader aspects is not limited to the specific details, representative devices and methods, and illustrative examples shown and described. Departures may be made from such without departing from the spirit or scope of the general inventive concept as defined by the appended claims and their equivalents.

The invention claimed is:

1. A method for inspecting a surface of a semiconductor workpiece, the method comprising:
providing a surface inspection system and using the surface inspection apparatus to cause laser light to impinge upon a test location on the workpiece surface and thereby cause the laser light to emerge from the surface as returned light comprising at least one of reflected light and scattered light;
collecting the returned light and generating a signal from the returned and collected light, the signal comprising a signal value representative of a characteristic of the workpiece surface at the test location;
providing a plurality of defect threshold candidates, the violation of which indicates the presence of a preexisting defect on the workpiece,
receiving with the surface inspection system an input from a user, where the input represents a desired sensitivity for the inspection of the workpiece,
causing the surface inspection system to automatically select a threshold from among the plurality of defect threshold candidates based on the input from the user and a plurality of prior signal values from secondary test locations, such that the threshold selected for the test location is different from the threshold selected for a different test location on the workpiece;
comparing the threshold to the signal value to obtain a difference value;
using the difference value to assess the characteristic of the workpiece surface at the test location; and
using the surface inspection system to automatically cause the method to be repeated for a plurality of test locations on the workpiece surface.

2. A method as recited in claim 1, wherein the collected and returned light consists of scattered light.

3. A method as recited in claim 1, wherein the collected and returned light consists of reflected light.

4. A method as recited in claim 1, wherein the plurality of threshold candidates comprises an estimate of the signal value.

5. A method as recited in claim 1, wherein the plurality of threshold candidates comprises a statistical value based upon a plurality of signal values for a corresponding plurality of test locations on the workpiece surface.

6. A method as recited in claim 1, wherein the plurality of threshold candidates comprises a value that is representative of a minimum size expected for the characteristic that is detectable given the sensitivity of the surface inspection system.

7. A method as recited in claim 6, further comprising using a constant sensitivity value to comprise the plurality of threshold candidates.

8. A method as recited in claim 1, wherein the plurality of threshold candidates comprises a false alarm-based threshold that is representative of a minimum size expected for the characteristic that is detectable given the sensitivity of the surface inspection system and a desired maximum probability of false identifications of the characteristic in the signal value for the surface inspection system.

9. A method as recited in claim 1, wherein the plurality of threshold candidates comprises a false alarm-based threshold that is representative of a maximum acceptable probability of false defect detection for the surface inspection system.

10. A system for inspecting a surface of a semiconductor workpiece, the system comprising:
a laser source that causes a laser light to impinge upon a test location on the workpiece surface and thereby cause the laser light to emerge from the surface as returned light comprising at least one of reflected light and scattered light;
a collection subsystem that collects the returned light and generates a signal from the returned and collected light, the signal comprising a signal value representative of a characteristic of the workpiece surface at the test location;
a processing device that, receives an input from a user, where the input represents a desired sensitivity for the inspection of the workpiece, causes the system to automatically select a threshold from among a plurality of defect threshold candidates, the violation of which indicates the presence of a preexisting defect on the workpiece, based on the input from the user and a plurality of prior signal values from secondary test locations, such that the threshold selected for the test location is different from the threshold selected for a different test location on the workpiece, compares the signal value to the threshold to obtain a difference value, that uses the threshold using the difference value to assess the characteristic of the workpiece surface at the test location; and uses the surface inspection system to automatically analyze the workpiece surface at a plurality of test locations.

* * * * *